United States Patent
Alanine et al.

[11] Patent Number: 5,889,026
[45] Date of Patent: Mar. 30, 1999

[54] 4-HYDROXY-PIPERODINE DERIVATIVES

[75] Inventors: Alexander Alanine, Riedisheim, France; Bernd Büttelmann, Schopfheim, Germany; Marie-Paule Heitz Neidhart, Hagenthal Le Bas; Emmanuel Pinard, St. Louis, both of France; René Wyler, Zurich, Switzerland

[73] Assignee: Hoffmann-La Roche Inc., Nutley, N.J.

[21] Appl. No.: 891,781

[22] Filed: Jul. 14, 1997

[30] Foreign Application Priority Data

Jul. 19, 1996 [EP] European Pat. Off. ............... 96111660
Apr. 1, 1997 [EP] European Pat. Off. ............... 97105366

[51] Int. Cl.$^6$ .......................... C07D 211/00; A01N 43/40
[52] U.S. Cl. ....................... 514/326; 514/327; 546/340.1; 546/366; 546/370
[58] Field of Search ................... 546/340.1, 370, 546/366; 514/327, 326

[56] References Cited

FOREIGN PATENT DOCUMENTS

| | | |
|---|---|---|
| 0 441 506 A2 | 8/1991 | European Pat. Off. . |
| 0 648 744 A1 | 4/1995 | European Pat. Off. . |
| 2 672 286 | 8/1992 | France . |
| 2 681 319 | 3/1993 | France . |
| 95/20587 | 8/1995 | WIPO . |
| 97/23215 | 7/1997 | WIPO . |
| WO 97/23216 | 7/1997 | WIPO . |

OTHER PUBLICATIONS

Chemical Abstracts AN 1973:43277, Mauyama et al., Dec. 1972.
Chenard, B.L., et al., *J. Med. Chem.*, 34(10):3085–3090 (1991).
Derwent Abstract of FR 2,672,286 (corresponds to Document B4), (Aug. 7, 1992).
Derwent Abstract of FR 2,681,319 (corresponds to Document B5), (Mar. 19, 1993).

Green, T., Protective Groups in Organic Synthesis Chapter 7, John Wiley & Sons, Inc. (1981) pp. 218–287.
Hollmann & Heinemann, (1994) Annu. Rev. Neurosci. 17:31.
Sigel, et al., J. Biol. Chem. 269:8204 (1994).
Malherbe, et al., Mol. Brain Res. 8:199 (1990).
Methfessel et al., Pflügers Arch. 407:577 (1986).

*Primary Examiner*—Keith D. MacMillan
*Attorney, Agent, or Firm*—George W. Johnston; Dennis P. Tramaloni; Alan P. Kass

[57] ABSTRACT

The present invention relates to compounds of the formula

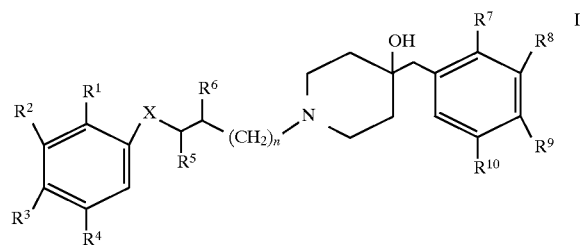

wherein x is —O—, —NH—, —CH$_2$—, —CH=, —CO$_2$—, —CONH—, —CON(lower alkyl)—, —S— and —SO$_2$—;

$R^1$–$R^4$ are, independently from each other hydrogen, halogen, hydroxy, amino, nitro, lower-alkyl-sulfonylamido, 1- or 2-imidazolyl, 1-(1,2,4-triazolyl) or acetamido;

$R^5$, $R^6$ are, independently from each other hydrogen, lower-alkyl, hydroxy, lower alkoxy or oxo;

$R^7$–$R^{10}$ are, independently from each other hydrogen, lower-alkyl, halogen, trifluoromethyl or lower-alkoxy;

n is 0 or 1;

and to pharmaceutically acceptable acid addition salts thereof. Compounds of the present invention are NMDA(N-methyl-D-aspartate)-receptor subtype selective blockers.

22 Claims, No Drawings

4-HYDROXY-PIPERODINE DERIVATIVES

BACKGROUND OF THE INVENTION

FIELD OF THE INVENTION

The invention relates to 4-hydroxy-piperidine derivatives useful in treating neurodegeneration.

BRIEF SUMMARY OF THE INVENTION

The present invention relates to compounds of the formula

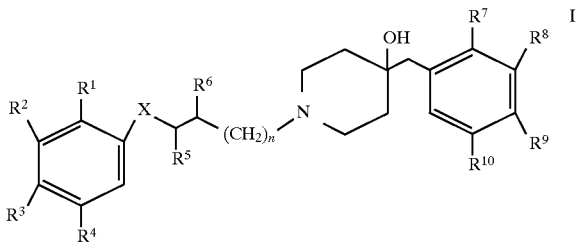

wherein x is —O—, —NH—, —CH$_2$—, —CH═, —CO$_2$—, —CONH—, —CON(lower alkyl)—, —S— and —SO$_2$—;

$R^1$–$R^4$ are, independently, hydrogen, halogen, hydroxy, amino, nitro, lower-alkyl-sulfonylamido, 1- or 2-imidazolyl, 1-(1,2,4-triazolyl) or acetamido;

$R^5$, $R^6$ are, independently, hydrogen, lower-alkyl, hydroxy, lower alkoxy or oxo;

$R^7$–$R^{10}$ are, independently, hydrogen, lower-alkyl, halogen, trifluoromethyl or lower-alkoxy;

n is 0 or 1;

and to pharmaceutically acceptable acid addition salts thereof.

The compounds of formula I and their salts are distinguished by valuable therapeutic properties. Compounds of the present invention are NMDA(N-methyl-D-aspartate)-receptor subtype selective blockers, which have a key function in modulating neuronal activity and plasticity which makes them key players in mediating processes underlying development of CNS, as well as, learning and memory formation.

Under pathological conditions of acute and chronic forms of neurodegeneration, overactivation of NMDA receptors is a key event for triggering neuronal cell death. NMDA receptors are composed of members from two subunit families, namely NR-1 (8 different splice variants) and NR-2 (A to D) originating from different genes. Members from the two subunit families show a distinct distribution in different brain areas. Heteromeric combinations of NR-1 members with different NR-2 subunits result in NMDA receptors displaying different pharmaceutical properties. Thus, NMDA receptor subtype specific blockers are useful in treating acute forms of neurodegeneration caused, for example, by stroke and brain trauma, and chronic forms of neurodegeneration such as Alzheimer,s disease, Parkinson,s disease, Huntington,s disease, ALS (amyotrophic lateral sclerosis) and neurodegeneration associated with bacterial or viral infections.

Objects of the invention are the compounds of formula I and pharmaceutically acceptable acid addition salts thereof, the preparation of the compounds of formula I and salts thereof, medicaments containing a compound of formula I or a pharmaceutically acceptable acid addition salt thereof, the manufacture of such medicaments and the use of the compounds of formula I and their pharmaceutically acceptable salts in the control or prevention of illnesses, especially of illnesses and disorders of the kind referred to earlier, and, respectively, for the manufacture of corresponding medicaments.

DETAILED DESCRIPTION OF THE INVENTION

The present invention relates to compounds of the formula

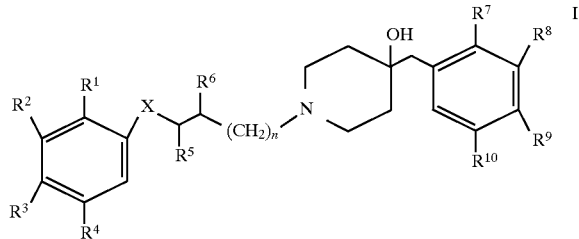

wherein x is —O—, —NH—, —CH$_2$—, —CH═, —CO$_2$—, —CONH—, —CON(lower alkyl)—, —S— and —SO$_2$—;

$R^1$–$R^4$ are, independently hydrogen, halogen, hydroxy, amino, nitro, lower-alkyl-sulfonylamido, 1- or 2-imidazolyl, 1-(1,2,4-triazolyl) or acetamido;

$R^5$, $R^6$ are, independently, hydrogen, lower-alkyl, hydroxy, lower alkoxy or oxo;

$R^7$–$R^{10}$ are, independently, hydrogen, lower-alkyl, halogen, trifluoromethyl or lower-alkoxy;

n is 0 or 1;

and to pharmaceutically acceptable acid addition salts thereof.

The following definitions of the general terms used in the present description apply irrespective of whether the terms in question appear alone or in combination.

As used herein, the term "lower alkyl" denotes a straight- or branched-chain alkyl group containing from 1 to 4 carbon atoms, for example, methyl, ethyl, propyl, isopropyl, butyl and the like.

The term "halogen" denotes chlorine, iodine, fluorine and bromine.

The term "lower alkoxy" denotes a group wherein the alkyl residue is as defined above.

The term "leaving group" has the meaning conventionally used, and refers to, for example, halogen, alkylsulfonyloxy, arylsulfonyloxy and the like. The most preferred leaving group in the present case is a halogen.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid and the like.

The compounds of formula I, in which either $R^5$ or $R^6$ or both are different from hydrogen and represent a hydroxy or lower alkyl group, contain at least one asymmetric carbon atom. Accordingly, the formation of two diastereomers is possible. The present invention embraces racemic mixtures and their corresponding enantiomers.

In a preferred embodiment, when X in a compound of formula I is O, $R^1$ is hydrogen, $R^2$ is hydrogen, $R^3$ is hydroxy or lower alkyl-sulfonylamido, $R^4$ is hydrogen, $R^5$ is hydrogen, $R^6$ is hydroxy, hydrogen or lower alkyl, $R^7$ is hydrogen, $R^8$ is hydrogen, $R^9$ is hydrogen, lower alkyl or halogen, $R^{10}$ is hydrogen and n is 0 or 1.

Exemplary preferred compounds in which X denotes O, are:

1-[2-(4-hydroxy-phenoxy)-ethyl]-4-(4-methyl-benzyl)-piperidin-4-ol;

4-(4-fluoro-benzyl)- 1-[2-(4-hydroxy-phenoxy)-ethyl]-piperidin-4-ol;

N-(4-{2-[4-hydroxy-4-(4-methyl-benzyl)-piperidin- 1-yl]-ethoxy}-phenyl)-methanesulfonamide;

N-(4-{2-[4-(4-fluoro-benzyl)-4-hydroxy-piperidin-1-yl]-ethoxy}-phenyl)-methanesulfonamide;

N-(4-{2-[4-(4-chloro-benzyl)-4-hydroxy-piperidin-1-yl]-ethoxy}-phenyl)-methanesulfonamide;

N-(4-{3-[4-(4-fluoro-benzyl)-4-hydroxy-piperidin- 1-yl]-propoxy}-phenyl)-methanesulfonamide;

(RS)-1-[2-(4-hydroxy-phenoxy)-1-methyl-ethyl]-4-(4-methyl-benzyl)-piperidin-4-ol.

In another preferred embodiment, when X in a compound of formula I is NH, $R^1$, $R^2$, $R^4$, $R^6$, $R^7$, $R^8$ and $R^{10}$ are hydrogen, $R^3$ is hydroxy, $R^5$ is oxo, $R^9$ is hydrogen or lower alkyl and n is 0 or 1.

Exemplary preferred compounds in which X denotes NH, are:

2-(4-benzyl-4-hydroxy-piperidin-1-yl)-N-(4-hydroxy-phenyl)-acetamide;

2-[4-hydroxy-4-(4-methyl-benzyl)-piperidin- 1-yl]-N-(4-hydroxy-phenyl)-acetamide.

In another preferred embodiment, when X in a compound of formula I is $CH_2$, $R^1$, $R^2$, $R^4$, $R^6$, $R^7$, $R^8$ and $R^{10}$ are hydrogen, $R^3$ is hydroxy, $R^5$ is hydroxy, $R^9$ is hydrogen or lower alkyl and n is 0.

Other exemplary preferred compounds in which X denotes $CH_2$ are:

(RS)-4-benzyl-1-[2-hydroxy-3-(4-hydroxy-phenyl)-propyl]-piperidin-4-ol;

(RS)-1-[2-hydroxy-3-(4-hydroxy-phenyl)-propyl]-4-(4-methyl-benzyl)-piperidin-4-ol;

(RS)-4-(4-chloro-benzyl)-1-[2-hydroxy-3-(4-hydroxy-phenyl)-propyl ]-piperidin-4-ol.

The present compounds of formula I and their pharmaceutically acceptable salts can be prepared by methods known in the art, for example, by processes described below, which comprise a) reacting a compound of the formula

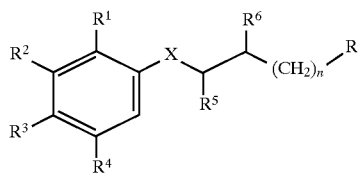

with a compound of the formula

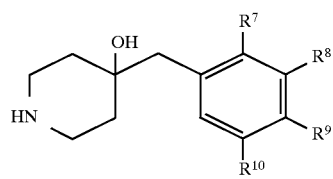

wherein $R^1$–$R^{10}$ and X have the significances given above, n is 1, R is a leaving group and $R^6$ is an oxo- or a hydroxy group, or b) reacting a compound of the formula

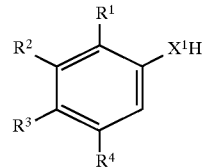

with a compound of the formula

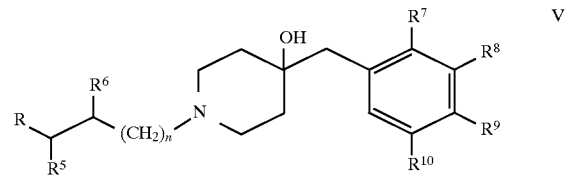

wherein $R^1$–$R^{10}$, n and R have the significances given above and $X^1$ is —O—, —NH—, —N—lower alkyl— or —S—, or c) reacting a compound of the formula

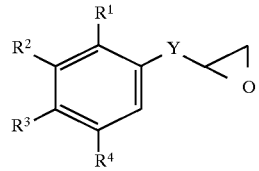

with a compound of the formula III to give a compound of the formula

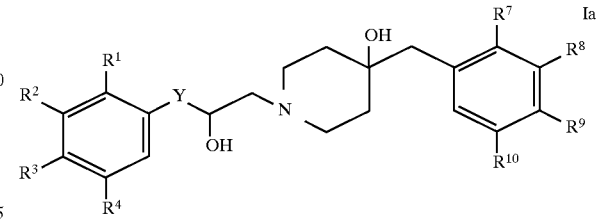

wherein $R^1$–$R^4$ and $R^7$–$R^{10}$ have the significances given above, and Y denotes—$XCH_2$— or —$CH_2$—, or d) reacting a compound of the formula IV with a compound of the formula

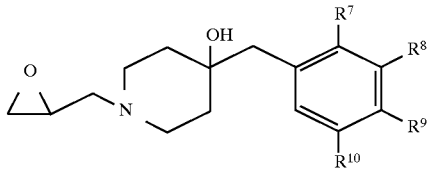

to give a compound of the formula Ia, wherein $R^1$–$R^4$ and $R^7$–$R^{10}$ have the significances given above, or e) debenzylating a compound of the formula

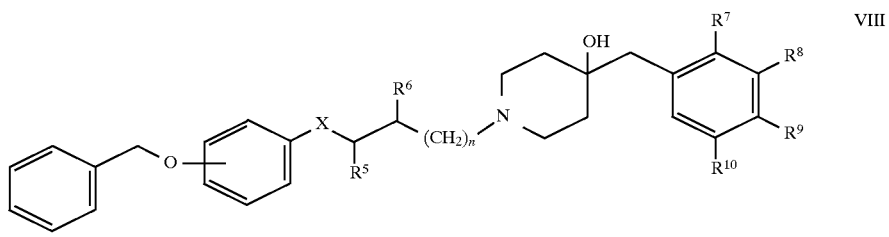

wherein the substituents are as described above, provided that none of $R^7$–$R^{10}$ is halogen, or f) reacting a compound of formula I wherein one of $R^1$–$R^4$ is an amino group with a lower-alkyl-sulfonyl halogen to give a compound of formula I, wherein one of $R^1$–$R^4$ is a lower alkyl-sulfonyl-amino group, or g) reducing a compound of formula I, wherein $R^5$ and/or $R^6$ represents a carbonyl group, to yield the corresponding hydroxy compound, or h) oxidizing a compound of formula I, wherein X represents —S—, to yield the corresponding sulfonyl (—$SO_2$—) compound, or i) cleaving off (a) hydroxy or amino protecting group(s) present as (a) substituent(s) $R^1$–$R^4$, and j) if desired, converting the compound of formula I obtained into a pharmaceutically acceptable acid addition salt.

In accordance with process variant a) a mixture of a compound of formula III, for example 4-(4-methyl-benzyl)-piperidin-4-ol, and of a compound of formula II, for example, N-[4-(2-bromoethoxy)-phenyl]-methansulfonamide, dissolved in 2-butanone, is refluxed about 12 hours. This reaction is carried out in the presence of a base, for example, potassium carbonate. The compound of formula I is then separated in conventional manner. When one of $R^1$–$R^4$ in formula II is a hydroxy group these groups are protected by groups conventionally used.

Examples of such groups are described in Green, T., Protective Groups in Organic Synthesis, Chapter 7, John Wiley and Sons, Inc. (1981) pp. 218–287. Most preferred are the benzyloxy, tert-butyl-dimethyl-silyloxy or ethyloxycarbonyl groups. This reaction can be carried out by known methods.

Process variant b) describes a process to obtain compounds of formula I by reaction of a compound of formula IV with a compound of formula V.

Preferred compounds of formula IV are the corresponding phenoles and amines.

This reaction is carried out in the presence of a base. Preferred is potassium carbonate. The reaction is refluxed for about 12 hours in a suitable solvent, such as 2-butanone and the yielded compound is then separated in conventional manner.

In accordance to process variant c) a corresponding oxiranyl-phenyl derivative of formula VI is treated with a compound of formula III to give a corresponding compound of formula Ia. This reaction is carried out in a suitable solvent, such as methanol or ethanol.

Variant e) describes a process to obtain compounds of formula I, wherein one of $R^1$–$R^4$ is hydroxy. This process is carried out by debenzylating a compound of formula VIII, provided that none of $R^7$–$R^{10}$ is halogen. The debenzylation is carried out in conventional manner. For example, a compound of formula VIII is dissolved in a suitable solvent or mixture of solvents, such as ethanol and ethylacetate, and hydrogenated in the presence of Pd on C at room temperature and atmospheric pressure.

In accordance with process variant f) a compound of formula I can be obtained, wherein one of $R^1$–$R^4$ is a lower-alkyl-sulfonyl-amino group. This reaction is carried out by treating a compound of formula I, wherein one of $R^1$–$R^4$ is an amino group, for example (RS)-1-[3-(4-amino-phenoxy)-2-hydroxy-propyl]-4-benzyl-piperidin-4-ol, with a lower-alkyl-sulfonylhalogen, such as methane sulfonylchloride, in a suitable solvent, such as methylene chloride, in the presence of pyridine at room temperature.

The process variant g) describes the reduction of a compound of formula I, wherein $R^5$ and/or $R^6$ represents a carbonyl group to yield the corresponding hydroxy group. This process is carried out in the presence of a metal hydride, such as $LiAlH_4$, in conventional manner.

In accordance with process variant h) a compound of formula I, wherein X represents —S—, is oxidized to yield the corresponding sulfonyl ($SO_2$—) compound. The oxidation can be carried out in the presence of Oxone® (potassium monopersulfate triple salt) at room temperature.

Suitable protecting groups and methods for their cleavage will be familiar to any person skilled in the art, although of course there can be used only those protecting groups which can be cleaved off by methods under the conditions of which other structural elements in the compounds are not affected.

The acid addition salts of the compounds of formula I are especially well suited for pharmaceutical use.

The starting materials for the preparation of compounds of formula I are known or can be prepared by known methods, for example, according to the following reaction schemes 1–5. These reactions are described in more detail in examples 34–70.

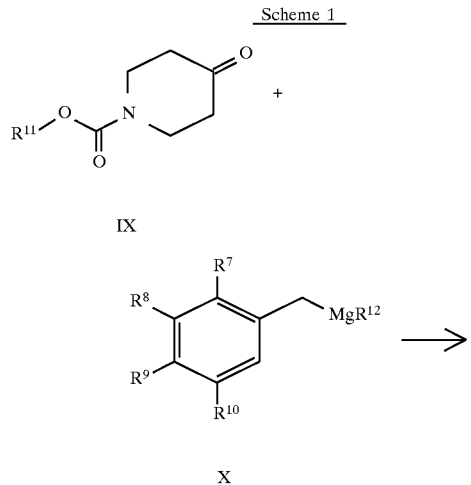

-continued
Scheme 1
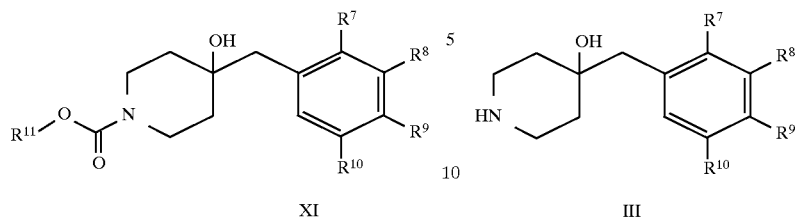
wherein $R^7$–$R^{10}$ is as above, $R^{11}$ is lower alkyl, and $R^{12}$ is Cl, Br or I.
Scheme 2
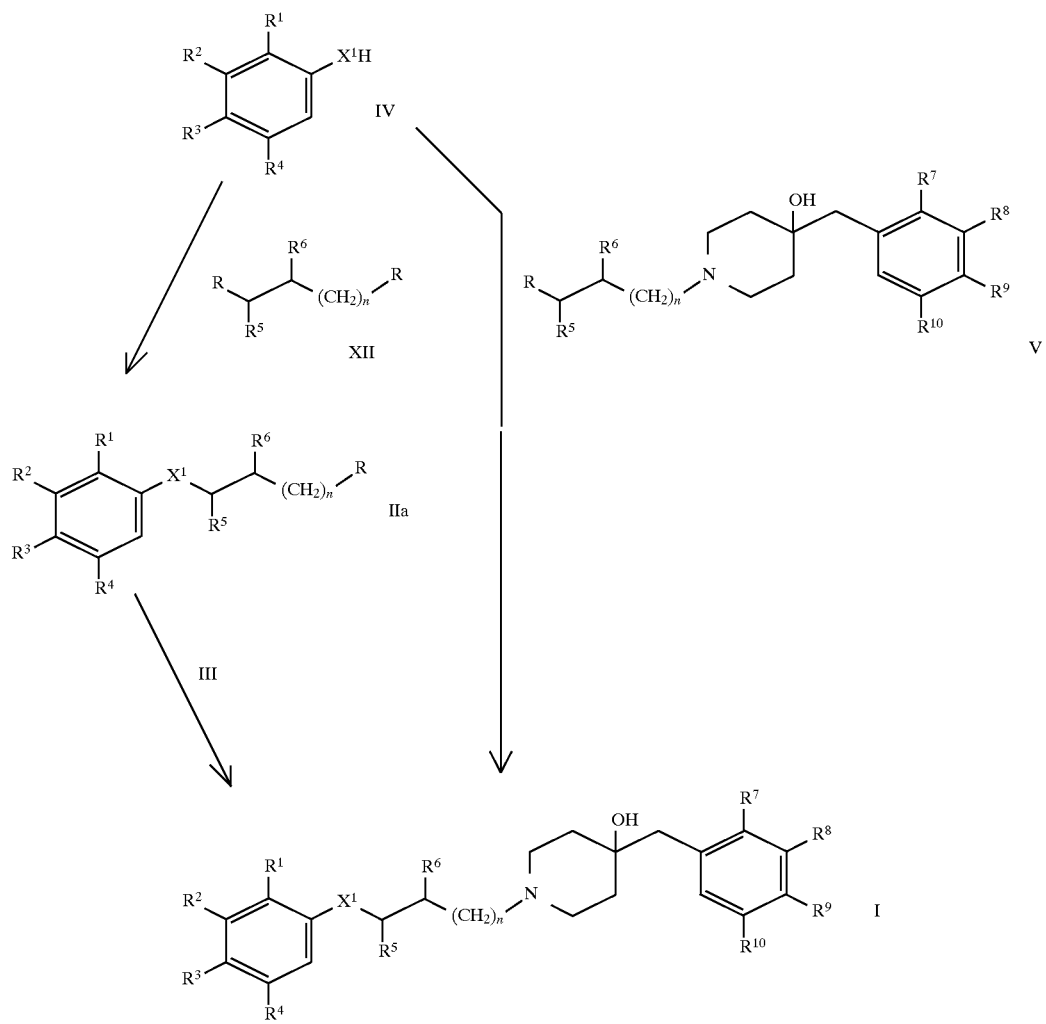
wherein R is a leaving group, $R^1$–$R^5$, and $R^7$–$R^{10}$ have the significances given above, $R^6$ is =O or OH, n is 1 and $X^1$ is —O—, —NH— or —S—.

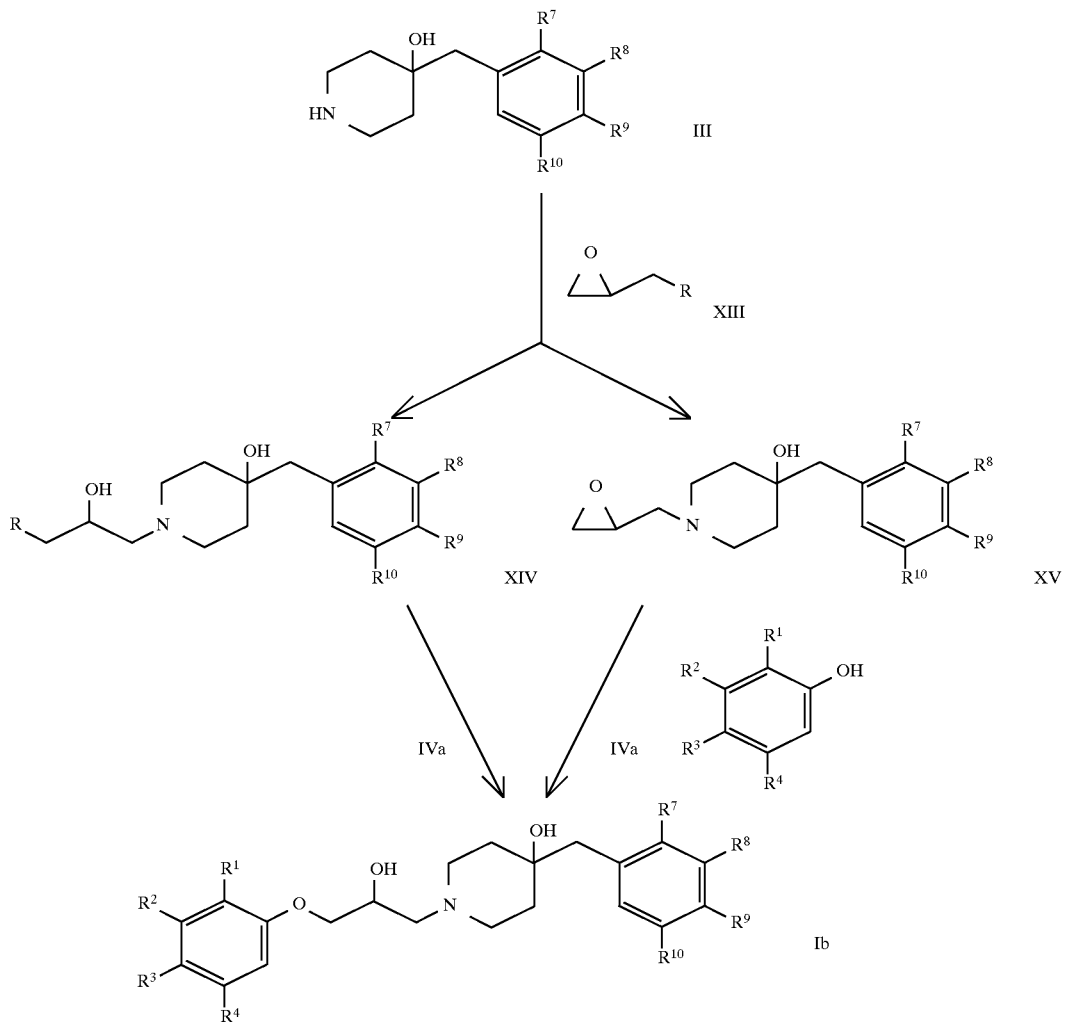
wherein R, $R^1$–$R^4$ and $R^7$–$R^{10}$ are described as above.
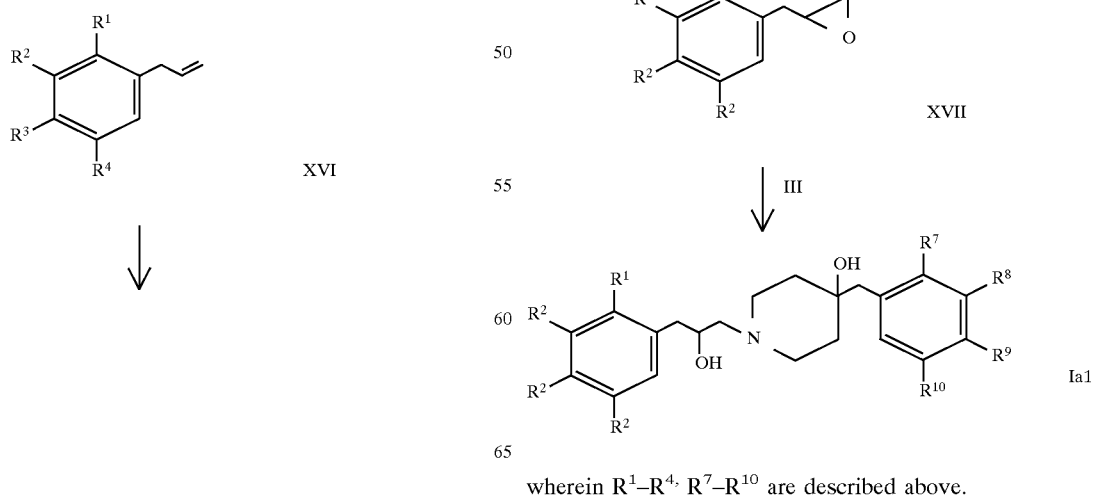
wherein $R^1$–$R^4$, $R^7$–$R^{10}$ are described above.

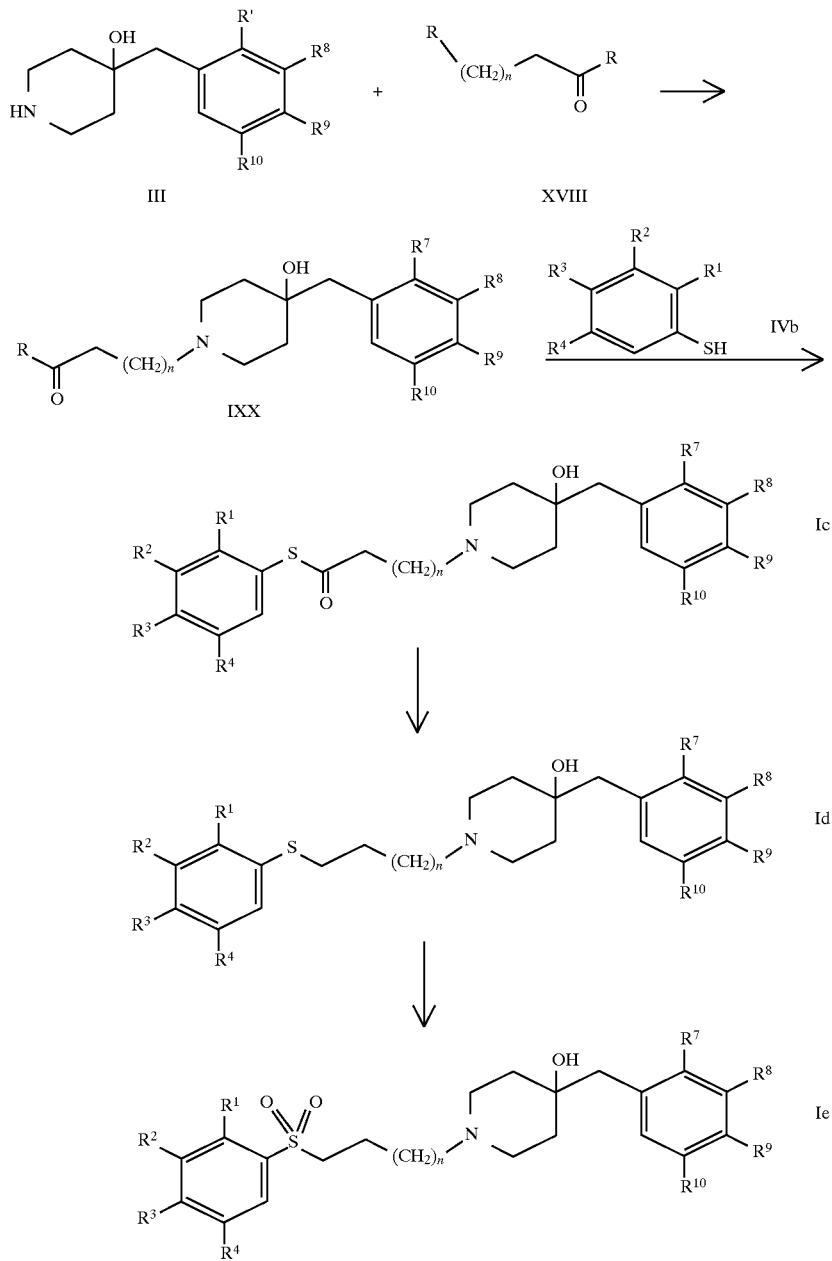

wherein R, $R^1$–$R^4$, $R^7$–$R^{10}$ and n have the significances given above.

As mentioned earlier, the compounds of formula I and their pharmaceutically usable acid addition salts possess valuable pharmacodynamic properties. They are NMDA-receptor subtype selective blockers, which have a key function in modulating neuronal activity and plasticity which makes them key players in mediating processes underlying development of CNS as well as learning and memory formation.

The compounds were investigated in accordance with the tests given hereinafter.

Method 1

3H-Ro 25-6981 binding (Ro 25-6981 is [R—(R*,S*)]-a-(4-Hydroxy-phenyl)-b-methyl-4-(phenyl-methyl)-1-piperidine propanol)

Male Füllinsdorf albino rats weighing between 150–200 g were used. Membranes were prepared by homogenization of the whole brain minus cerebellum and medulla oblongata with a Polytron (10.000 rpm, 30 seconds), in 25 volumes of a cold Tris-HCl 50 mM, ethylene diamine tetraacetic acid (EDTA) 10 mM, pH 7.1 buffer. The homogenate was centrifuged at 48.000 g for 10 minutes at 4° C. The pellet was resuspended using the Polytron in the same volume of buffer and the homogenate was incubated at 37° C. for 10 minutes. After centrifugation, the pellet was homogenized in the same buffer and frozen at −80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 mg of protein/ml.

3H-Ro 25-6981 binding experiments were performed using a Tris-HCl 50 mM, pH 7.4 buffer. For displacement experiments 5 nM of 3H-Ro 25-6981 were used and non specific binding was measured using 10 mM of tetrahydroisoquinoline and usually it accounts for 10% of the total. The incubation time was 2 hours at 4° C. and the assay was stopped by filtration on Whatmann GF/B glass fiber filters (Unifilter-96, Packard, Zürich, Switzerland). The filters were washed 5 times with cold buffer. The radioactivity on the filter was counted on a Packard Top-count microplate scintillation counter after addition of 40 mL of microscint 40 (Canberra Packard S. A., Zürich, Switzerland).

The effects of compounds were measured using a minimum of 8 concentrations and repeated at least once. The pooled normalized values were analyzed using a non-linear regression calculation program which provide $IC_{50}$ with their relative upper and lower 95% confidence limits (RS1, BBN, USA).

Method 2
3H-Prazosine binding

Male Fullinsdorf albino rats weighing between 150–200 g were used. Membranes were prepared by homogenization of the whole brain minus cerebellum and medulla oblongata with a Plytron (10.000 rpm, 30 seconds), in 25 volumes of a cold Tris-HCl 50 mM, EDTA 10 mM, pH 7.1 buffer. The homogenate was centrifuged at 48.000 g for 10 minutes at 4° C. The pellet was resuspended using the Polytron in the same volume of buffer and the homogenate was incubated at 37° C. for 10 minutes. After centrifugation, the pellet was homogenized in the same buffer and frozen at -80° C. for at least 16 hours but not more than 10 days. For the binding assay the homogenate was thawed at 37° C., centrifuged and the pellet was washed three times as above in a Tris-HCl 5 mM, pH 7.4 cold buffer. The final pellet was resuspended in the same buffer and used at a final concentration of 200 mg of protein/ml.

3H-Prazosine binding experiments were performed using a Tris-HCl 50 mM, pH 7.4 buffer. For displacement experiments 0.2 nM of 3H-Prazosine were used and non specific binding was measured using 100 mM of Chlorpromazine. The incubation time was 30 minutes at room temperature and the assay was stopped by filtration on Whatman GF/B glass fiber filters (Unifilter-96, Canberra Packard S. A., Zürich, Switzerland). The filters were washed 5 times with cold buffer. The radioactivity on the filter was counted on a Packard Top-count microplate scintillation counter after addition of 40 ml of microscint 40 (Canberra Packard S. A., Zürich, Switzerland). The effects of compounds were measured using a minimum of 8 concentrations and repeated at least once. The pooled normalized values were analyzed using a non-linear regression calculation program which provide $IC_{50}$ with their relative upper and lower 95% confidence limits (RS1, BBN, USA).

Method 3
Electrophysiology on recombinant NMDA receptors cDNA clones coding for the subunits NMDAR1C and NMDAR2A of the NMDA receptor (see Hollmann and Heinemann, 1994, Annu. Rev. Neurosci. 17:31 for nomenclature of NMDA receptor subunits) were isolated from a rat brain lgt11 cDNA library as published elsewhere (Sigel et al., 1994, J. Biol. Chem. 269:8204). The clone for the subunit NMDAR2B of the rat brain NMDA receptor was obtained from S. Nakanishi (Kyoto, Japan). The cDNAs were transcribed, capped and poly(A⁺)-tailed as described previously (Malherbe et al., 1990, Mol. Brain Res. 8: 199). Oocytes of South African frogs (Xenopus laevis) were used for expressing either a combination of the NMDAR1C and NMDAR2A subunits or the NMDAR1C and NMDAR2B subunits. Approximately 3 fmol of a 1:1 mixture of the respective MRNA species were injected into every oocyte. Four to five days later, the ion current through the NMDA receptor channels was measured in voltage clamp experiments (see Methfessel et al., 1986, Pflügers Arch. 407:577 for the methods of oocyte expression and voltage-clamping). The membrane potential was clamped to -80 mV and the receptors were activated by applying a modified Ringer,s solution containing the NMDA-receptor agonists L-asparatate (Asp) and glycine (Gly). Different agonist concentrations were chosen for either subunit combination to account for the different agonist sensitivities of the two types of receptors (70 mM Asp plus 2.5 mM Gly for NMDAR1C-NMDAR2A and 15 mM Asp plus 0.2 mM Gly for NMDAR1C-NMDAR2B). The agonists were applied for 15 s intervals once every 2.5 min by rapid superfusion of the oocyte with agonist containing solution and the amplitude of the agonist-evoked current was measured immediately before the end of each application. After a series of initial control applications, the antagonist to be tested was added to both, the basal Ringer,s and the agonist containing solution. The antagonist concentration applied to oocytes expressing the NR2A subunit was 10 mmol/l, whereas 0.1 mmol/l were applied to the NR2B expressing oocytes. Four to eight oocytes were tested for every compound and NMDA receptor subtype. Oocytes were exposed to the compounds for 5 to 30 min depending on the time needed for reaching an equilibrium block of the NMDA receptor current. For every oocyte the decrease of the current amplitude was expressed as a percentage of the control current measured before application of the compound. Figures in the table are arithmetic mean values of these percentage values. The thus-determined activity of some compounds in accordance with the invention will be evident from the following table.

TABLE 1

| Com- pound/ Example | 3H-Ro 25-6981 binding $IC_{50}$ ($\mu$M) | 3H-prazosine binding $IC_{50}$ ($\mu$M) | Electrophysiology, % block by | |
|---|---|---|---|---|
| | | | 10 $\mu$M NR1C + NR2A | 0.1 $\mu$M NR1C + NR2B |
| A/1 | 0.015 | 1.5 | 29 | 96 |
| B/5 | 0.060 | 4.0 | | |
| C/9 | 0.010 | 3.5 | 31 | 88 |
| D/10 | 0.040 | 3.0 | | |
| E/11 | 0.030 | 5.0 | 27 | 91 |
| F/12 | 0.060 | 6.0 | | |
| G/13 | 0.030 | 9.0 | | |
| H/14 | 0.040 | 1.8 | | |
| I/22 | 0.040 | 2.5 | | |
| J/23 | 0.070 | 20.0 | | |
| K/24 | 0.040 | 30.0 | 10 | 83 |
| L/30 | 0.060 | 7.4 | | |
| M/31 | 0.020 | 9.7 | 10 | 89 |
| N/32 | 0.040 | 9.2 | 19 | 81 |
| O/34 | 0.010 | 0.8 | | |
| P/35 | 0.003 | 0.26 | | |
| Q/36 | 0.010 | 5.0 | | |
| R/37 | 0.006 | 5.3 | 8 | 42 |
| S/38 | 0.016 | 7.3 | | |
| T/39 | 0.009 | 2.3 | | |
| V/41 | 0.008 | 3.0 | | |
| W/94 | 0.020 | 6.6 | | |

In this Table the respective compounds are:
A (RS)-1-[2-Hydroxy-3-(4-hydroxy-phenoxy)-propyl]-4(4-methyl-benzyl)-piperidin-4-ol;

B (S)-4-Benzyl-1-[2-hydroxy-3-(4-hydroxy-phenoxy)-propyl]-piperidin-4-ol;
C 1-[2-(4-Hydroxy-phenoxy)-ethyl]-4-(4-methyl-benzyl)-piperidin-4-ol;
D 4-(4-Fluoro-benzyl)-1-[2-(4-hydroxy-phenoxy)-ethyl]-piperidin-4-ol;
E N-(4-{2-[4-Hydroxy-4-(4-methyl-benzyl)-piperidin-1-yl]-ethoxy}-phenyl)-methanesulfonarnide;
F N-(4-{2-[4-(4-Fluoro-benzyl)-4-hydroxy-piperidin-1-yl]-ethoxy}-phenyl)-methanesulfonarnide;
G N-(4-{2-[4-(4-Chloro-benzyl)-4-hydroxy-piperidin-1-yl]-ethoxy}-phenyl)-methanesulfonamide;
H N-(4-{3-[4-(4-Fluoro-benzyl)-4-hydroxy-piperidin-1-yl]-propoxy}-phenyl)-methanesulfonamide;
I 1-[2-(4-Hydroxy-phenoxy)-1-methyl-ethyl]-4-(4-methyl-benzyl)-piperidin-4-ol;
J 2-(4-Benzyl-4-hydroxy-piperidin-1-yl)-N-(4-hydroxy-phenyl)-acetamide;
K 2-[4-Hydroxy-4-(4-methyl-benzyl)-piperidin-1-yl]-N-(4-hydroxy-phenyl)-acetamide;
L (RS)-4-Benzyl-1-[2-hydroxy-3-(4-hydroxy-phenyl)-propyl]-piperidin-4-ol;
M (RS)-1-[2-Hydroxy-3-(4-hydroxy-phenyl)-propyl]-4-(4-methyl-benzyl)-piperidin-4-ol;
N (RS)-4-(4-Chloro-benzyl)-1-[2-hydroxy-3-(4-hydroxy-phenyl)-propyl]-piperidin-4-ol;
O 4-Hydroxy-benzoic acid 2-[4-hydroxy-4-(4-methyl-benzyl)-piperidin-1-yl]ethylester;
P 4-Hydroxy-benzoic acid 3-[4-hydroxy-4-(4-methyl-benzyl)-piperidin-1-yl]-propylester;
Q N-[2-(4-Benzyl-4-hydroxy-piperidin-1-yl)-ethyl]-4-hydroxy-benzamide;
R 4-Hydroxy-N-[2-[4-hydroxy-4-(4-methyl-benzyl)-piperidin-1-yl]-ethyl]-benzamide;
S N-[3-(4-Benzyl-4-hydroxy-piperidin-1-yl)-propyl]-4-hydroxy-benzamide;
T 4-Hydroxy-N-[3-[4-hydroxy-4-(4-methyl-benzyl)-piperidin-1-yl]-propyl]-benzamide;
V (E)-1-[3-(4-Hydroxy-phenyl)-allyl]-4-(4-methyl-benzyl)-piperidin-4-ol;
W (RS)-1-[3-(3-Fluoro-4-hydroxy-phenyl)-2-hydroxy-propyl]-4-(4-methyl-benzyl)-piperidin-4-ol hydrochloride By screening, compounds of formula I could be identified as NMDA receptor subtype selective blockers and—for selected compounds—the preference for NMDAR-2B subunits could be demonstrated by eletrophysiological characterization using cloned NMDA receptor subtypes expressed oocytes.

The compounds of formula I and their salts, as herein described, can be incorporated into standard pharmaceutical dosage forms, for example, for oral or parenteral application with the usual pharmaceutical adjuvant materials, for example, organic or inorganic inert carrier materials, such as, water, gelatin, lactose, starch, magnesium stearate, talc, vegetable oils, gums, polyalkylene-glycols and the like. The pharmaceutical preparations can be employed in a solid form, for example, as tablets, suppositories, capsules, or in liquid form, for example, as solutions, suspensions or emulsions. Pharmaceutical adjuvant materials can be added and include preservatives, stabilizers, wetting or emulsifying agents, salts to change the osmotic pressure or to act as buffers. The pharmaceutical preparations can also contain other therapeutically active substances.

The daily dose of compounds of formula I to be administered varies with the particular compound employed, the chosen route of administration and the recipient. Representative of a method for administering the compounds of formula I is by the oral and parenteral type administration route. An oral formulation of a compound of formula I is preferably administered to an adult at a dose in the range of 150 mg to 1.5 g per day. A parenteral formulation of a compound of formula I is preferably administered to an adult at a dose in the range of 5 to 500 mg per day.

The following Examples illustrate the invention in more detail. All temperatures are given in degrees Celsius.

EXAMPLE 1

(RS)-1-[2-Hydroxy-3-(4-hydroxy-phenoxy)-propyl]-4-(4-methyl-benzyl)-piperidin-4-ol hydrochloride (RS)-1-[3-(4-benzyloxy-phenoxy)-2-hydroxy-propyl]-4-(4-methyl-benzyl)-piperidin-4-ol (0.75 g, 1.6 mmol) was dissolved in a mixture of ethanol (20 ml) and ethyl acetate (20 ml) and hydrogenated in the presence of Pd on C at room temperature and atmospheric pressure. After filtration and evaporation of the solvent, the residue was dissolved in ethanol (30 ml) and ethyl acetate (20 ml). 1.1 Equivalent of ethanolic HCl were added to give (RS)-1-[2-hydroxy-3-(4-hydroxy-phenoxy)-propyl]-4-(4-methyl-benzyl)-piperidin-4-ol hydrochloride (0.38 g, 58%) as colorless solid mixture of the E/Z isomers, m.p. 93°–96° C. and MS: m/e=372.5 (M+H$^+$).

Following the general method of Example 1, the compounds of Example 2 to Example 5 were prepared.

EXAMPLE 2

(RS)-4-Benzyl-1-[2-hydroxy-3-(4-hydroxy-phenoxy)-propyl]-piperidin-4-ol hydrochloride The title compound, m.p. 89°–91° C. and MS: m/e=358.4 (M+H$^+$), was prepared from (RS)-4-benzyl-1-[3-(4-benzyloxy-phenoxy)-2-hydroxy-propyl]-piperidin-4-ol.

EXAMPLE 3

(RS)-4-(4-Fluoro-benzyl)-1-[2-hydroxy-3-(4-hydroxy-phenoxy)-propyl]-piperidin-4-ol hydrochloride The title compound, m.p. 199°–202° C. and MS: m/e=376.4 (M+H$^+$), was prepared from (RS)-1-[3-(4-benzyloxy-phenoxy)-2-hydroxy-propyl]-4-(4-fluoro-benzyl)-piperidin-4-ol.

EXAMPLE 4

(R)-4-Benzyl-1-[2-hydroxy-3-(4-hydroxy-phenoxy)-propyl]-piperidin-4-ol hydrochloride The title compound, m.p. 77°–80° C., $[\alpha]_{365}^{20}$=+48.8° (c=1.0, methanol) and MS: m/e=358.5 (M+H$^+$), was prepared from from (R)-4-benzyl-1-[3-(4-benzyloxy-phenoxy)-2-hydroxy-propyl]-piperidin-4-ol.

EXAMPLE 5

(S)-4-Benzyl-1-[2-hydroxy-3-(4-hydroxy-phenoxy)-propyl]-piperidin-4-ol hydrochloride The title compound, m.p. 122°–125° C., $[\alpha]_{365}^{20}$=−48.0° (c=1.0, methanol) and MS: m/e=358.5 (M+H$^+$), was prepared from from (S)-4-benzyl-1-[3-(4-benzyloxy-phenoxy)-2-hydroxy-propyl]-piperidin-4-ol.

EXAMPLE 6

(RS)-4-Benzyl-1-[2-hydroxy-3-(4-nitro-phenoxy)-propyl]-piperidin-4-ol hydrochloride

[(4-Nitrophenoxy)methyl]-oxirane (1.9 g, 9.7 mmol) and 4-benzyl-4-hydroxy-piperidine (2.0 g, 10.7 mmol) were dissolved in ethanol (20 ml) and refluxed for 2 h. After evaporation of the solvent, the residue was chromatographed over silica gel (CH$_2$Cl$_2$-methanol (MeOH), 98:2). The crude, oily product was dissolved in ethyl acetate-ethanol (80 ml, 7:1) and 1.1 equivalent of ethanolic HCl were added to give (RS)-4-benzyl-1-[2-hydroxy-3-(4-nitro-phenoxy)-propyl]-piperidin-4-ol hydrochloride (3.4 g, 83%) as colourless solid mixture of the E/Z isomers, m.p. 104°–106° C. MS: m/e =387.4 (M+H$^+$).

EXAMPLE 7

(RS)-N-{4-[3-(4-Benzyl-4-hydroxy-piperidin-1-yl)-2-hydroxy-propoxy]-phenyl}-methanesulfonamide hydrochloide Methane sulfonylchloride (0.105 ml, 1.4 mmol) was added to a suspension of (RS)-1-[3-(4-amino-phenoxy)-2-hydroxy-propyl]-4-benzyl-piperidin-4-ol hydrochloride (0.5 g, 1.3 mmol) in CH$_2$Cl$_2$ (10 ml) and pyridine (5 ml) at room temperature. The mixture was stirred at room temperature overnight, water (15 ml) and brine (15 ml) were added and the mixture was extracted with CH$_2$Cl$_2$ (5×25 ml). The organic phases were pooled, dried with Na$_2$SO$_4$ and the solvent evaporated. The residue was chromatographed over silica gel (ethyl acetate-MeOH, 96:4) to give a colorless oil which was dissolved in ethanol (2 ml). 1.1 Equivalent of ethanolic HCl and t-butylmethylether (50 ml) were added to give (RS)-N-{4-[3-(4-benzyl-4-hydroxy-piperidin- 1-yl)-2-hydroxy-propoxy]-phenyl}-methanesulfonamide hydrochloride (0.24 g, 38%) as colorless solid mixture of the E/Z isomers, m.p. >230° C. dec and MS: m/e =435.4 (M+H$^+$).

EXAMPLE 8

4-Benzyl-1-[2-(4-hydroxy-phenoxy)-ethyl]-piperidin-4-ol hydrochloride

4-Benzyl-1-[2-(4-benzyloxy-phenoxy)-ethyl]-piperidin-4-ol (1.35 g, 3.2 mmol) was dissolved in a mixture of MeOH (75 ml) and ethyl acetate (75 ml) and hydrogenated in the presence of Pd on C at room temperature and atmospheric pressure. After filtration and evaporation of the solvent, the residue was dissolved in ethanol (2 mnl) and ethyl acetate (10 ml). 1.1 equivalent of ethanolic HCl were added to give 4-benzyl-1-[2-(4-hydroxy-phenoxy)-ethyl]-piperidin-4-ol hydrochloride (0.85 g, 72%) as colorless solid, m.p. 161°–163° C. and MS: m/e=328.3 (M+H$^+$).

Following the general method of Example 8, the compounds of Example 9 to Example 10 were prepared.

EXAMPLE 9

1-[2-(4-Hydroxy-phenoxy)-ethyl]-4-(4-methyl-benzyl)-piperidin-4-ol fumarate (1:0.5)

The title compound, m.p. 216°–218° C. and MS: mle=341 (M$^+$), was prepared from 1-[2-(4-benzyloxy-phenoxy)-ethyl]-4-(4-methyl-benzyl)-piperidin-4-ol.

EXAMPLE 10

4-(4-Fluoro-benzyl)-1-[2-(4-hydroxy-phenoxy)-ethyl]-piperidin-4-ol hydrochloride The title compound, m.p. 153°–155° C. and MS: m/e=345 (M$^+$), was prepared from 1-[2-(4-benzyloxy-phenoxy)-ethyl]-4-(4-fluoro-benzyl)-piperidin-4-ol.

EXAMPLE 11

N-(4-{2-[4-Hydroxy-4-(4-methyl-benzyl)-piperidin-1-yl]-ethoxy}-phenyl-methanesulfonamide hydrochloride A mixture of 4-(4-methyl-benzyl)-piperidin-4-ol (0.35 g, 1.7 mmol), N-[4-(2-bromethoxy)-phenyl]-methansulfonamide (0.5 g, 1.7 mmol) and potassium carbonate (0.25 g, 1.8 mmol) in 2-butanone (20 ml) was refluxed overnight. It was cooled to room temperature, 30 ml of H$_2$O were added and the organic phase was separated. The water phase was extracted two times with ethyl acetate. The organic phases were then pooled, dried with Na$_2$SO$_4$ and the solvent evaporated. The residue was chromatographed over silica gel (CH$_2$Cl$_2$—MeOH, 95:5) to give a yellowish foam which was dissolved in ethanol (5 ml) and ethyl acetate (10 ml). 1.1 Equivalent of ethanolic HCl were added to give N-(4-{2-[4-hydroxy-4-(4-methyl-benzyl)-piperidin-1-yl]-ethoxy}-phenyl)-methanesulfonamide hydrochloride (0.32 g, 41%) as colorless solid, m.p. >75°–78° C. dec. and MS: m/e=419.5 (M+H$^+$).

Following the general method of Example 11, the compounds of Example 12 to Example 14 were prepared.

EXAMPLE 12

N-(4-{2-[4-(4-Fluoro-benzyl)-4-hydroxy-piperidin-1-yl]-ethoxy}-phenyl )-methanesulfonamide hydrochloride The title compound, m.p. 131°–134° C. and MS: m/e=423.4 (M+H$^+$), was prepared from 4-(4-fluoro-benzyl)-piperidin-4-ol and N-[4-(2-bromethoxy)-phenyl]-methansulfonamide.

EXAMPLE 13

N-(4-{2-[4-(4-Chloro-benzyl)-4-hydroxy-piperidin-1 -yl]-ethoxy}-phenyl)-methanesulfonamide hydrochloride The title compound, m.p. 74°–77° C. and MS: m/e=439.4 (M+H$^+$), was prepared from 4-(4-chloro-benzyl)-piperidin-4-ol and N-[4-(2-bromoethoxy)-phenyl]-methansulfonamide.

EXAMPLE 14

N-(4-{3-[4-(4-fluoro-benzyl)-4-hydroxy-piperidin 1-yl]-propoxy}-phenyl)-methanesulfonamide hydrochloride The title compound MS: m/e=437.4 (M+H$^+$), was prepared from 4-(4-fluoro-benzyl)-piperidin-4-ol and N-[4-(2-bromopropoxy)-phenyl]-methansulfonamide.

EXAMPLE 15

(RS)-4-Benzyl-1-[2-hydroxy-3-(4-[1,2,4]triazol-1-yl-phenoxy)-propyl]-piperidin-4-ol hydrochloride A mixture of 4-benzyl-1-(3-chloro-2-hydroxy-propyl)-piperidin-4-ol (0.5 g, 1.8 mmol), 4,-(1H-1,2,4-triazol-1yl)-phenol (0.5 g, 1.8 mmol) and potassium carbonate (0.36 g, 2.6 mmol) in 2-butanone (20 ml) was refluxed overnight. It was cooled to room temperature, 50 ml of H$_2$O were added and the organic phase was separated. The water phase was extracted two times with ethyl acetate. The organic phases were then washed with 2N sodium hydroxide solution and pooled. The solution was dried with Na$_2$SO$_4$ and the solvent evaporated. The residue was dissolved in ethanol (10 ml) and ethyl acetate (50 ml). 1.1 Equivalent of ethanolic HCl were added to give (RS)-4-benzyl-1-[2-hydroxy-3-(4-[1,2,4]triazol-1-yl-phenoxy)-propyl]-piperidin-4-ol hydrochloride (0.69 g, 86%) as colorless solid mixture of the E/Z-isomers, m.p. 198°–200° C. and MS: m/e=409.5 (M+H$^+$).

EXAMPLE 16

(RS)-4-Benzyl-1-[2-hydroxy-3-(4-imidazol-1-yl-phenoxy)-propyl]-piperidin-4-ol hydrochloride The title compound, m.p.104°–108° C. and MS: n/e=408.6 (M+H$^+$), was prepared following the general method of Example 15 from 4-benzyl-1-(3-chloro-2-hydroxy-propyl)-piperidin-4-ol and 4-(1-imidazolyl)-phenol.

EXAMPLE 17

4-Benzyl-1-[3-(4-hydroxy-phenoxy)-propyl]-piperidin-4-ol hydrochloride

4-Benzyl-1-[3-(4-benzyloxy-phenoxy)-propyl]-piperidin-4-ol (0.432 g, 1 mmol) was dissolved in MeOH (50 ml) and hydrogenated in the presence of Pd on C at room temperature and atmospheric pressure. After filtration and evaporation of the solvent, the residue was dissolved in tetrahydrofuran (THF) (3 ml) and ether (10 ml). 1.1 equivalent of etheric HCl were added to give 4-benzyl-1-[3-(4-hydroxy-phenoxy)-propyl]-piperidin-4-ol hydrochloride (0.30 g, 88%) as colorless solid, m.p. 64° C. and MS: m/e=342.3 $(M+H^+)$.

Following the general method of Example 17, the compounds of Example 18 to Example 22 were prepared.

EXAMPLE 18

4-(4-Fluoro-benzyl)-1-[3-(4-hydroxy-phenoxy)-propyl]-piperidin-4-ol hydrochloride The title compound, MS: m/e=360.4 $(M+H^+)$, was prepared from 1-[3-(4-benzyloxy-phenoxy)-propyl]-4-(4-fluoro-benzyl)-piperidin-4-ol.

EXAMPLE 19

1-[3-(3-Hydroxy-phenoxy)-propyl]-4-(4-methyl-benzyl)-piperidin-4-ol hydrochloride The title compound, MS: m/e=356.4 $(M+H^+)$, was prepared from 1-[3-(3-benzyloxy-phenoxy)-propyl]-4-(4-methyl-benzyl)-piperidin-4-ol.

EXAMPLE 20

1-[3-(2-Hydroxy-phenoxy)-propyl]-4-(4-methyl-benzyl)-piperidin-4-ol hydrochloride The title compound, MS: m/e=356.4 $(M+H^+)$, was prepared from 1-[3-(2-benzyloxy-phenoxy)-propyl]-4-(4-methyl-benzyl)-piperidin-4-ol.

EXAMPLE 21

1-[2-(4-Hydroxy-phenoxy)-ethyl]-4-(4-methoxy-benzyl)-piperidin-4-ol hydrochloride The title compound, MS: m/e=358.3 $(M+H^+)$, was prepared from 1-[2-(4-benzyloxy-phenoxy)-ethyl]-4-(4-methoxy-benzyl)-piperidin-4-ol

EXAMPLE 22

1-[2-(4-Hydroxy-phenoxy)-1-methyl-ethyl]-4-(4-methyl-benzyl)-piperidin-4-ol hydrochloride The title compound, MS: m/e=356.3 $(M+H^+)$, was prepared from 1-[2-(4-benzyloxy-phenoxy)-1-methyl-ethyl]-4-(4-methoxy-benzyl)-piperidin-4-ol

EXAMPLE 23

2-(4-Benzyl-4-hydroxy-piperidin-1-yl)-N-(4-hydroxy-phenyl)-acetamide hydrochloride 2-(4-Benzyl-4-hydroxy-piperidin-1-yl)-N-[4-(tert-butyl-dimethyl-silanyloxy)-phenyl]-acetamide (0.454 g, 1 mmol) was dissolved in THF (6 ml) and stirred for 18 hours at room temperature in the presence of tetra-n-butylammonium fluoride/$SiO_2$ (1 g, 1.1 mmol, 1.1 mmol/g). The reaction mixture was quenched with 20% $NH_4Cl$ (20 ml) and the aqueous phase was extracted with ethyl acetate (3×5 ml). Combined organic phases were dried over $Na_2SO_4$ and concentrated. The residue was chromatographed over silica gel (hexan-ethyl acetate 1:1 then ethyl acetate) to give a foam which was dissolved in MeOH and treated with 1N HCl (0.9 ml). The solution was concentrated and the residue was refluxed in the presence of acetonitrile for 2 hours to provide, after cooling, 2-(4-Benzyl-4-hydroxy-piperidin-1-yl)-N-(4-hydroxy-phenyl)-acetamide-hydrochloride (0.27 g, 72%) as colorless solid mixture of the E/Z isomers, m.p. 222°–225° C. and MS: m/e=341.5 $(M+H^+)$.

Following the general method of Example 23 the compounds of Example 24 to Example 27 were prepared.

EXAMPLE 24

2-[4-Hydroxy-4-(4-methyl-benzyl)-piperidin-1-yl]-N-(4-hydroxy-phenyl)- acetamide hydrochloride The title compound, m.p. 242°–243° C. and MS: m/e=355.4 $(M+H^+)$, was prepared from N-[4-(tert-Butyl-dimethyl-silanyloxy)-phenyl]-2-[4-hydroxy-4-(4-methyl-benzyl)-piperidin-1-yl]-acetamide.

EXAMPLE 25

2-[4-(4-Chloro-benzyl)-4-hydroxy-piperidin-1-yl]-N-(4-hydroxy-phenyl)-acetamide hydrochloride The title compound, m.p. 205°–210° C. and MS: m/e=375.3 $(M+H^+)$, was prepared from N-[4-(tert-Butyl-dimethyl-silanyloxy)-phenyl]-2-[4-(4-chloro-benzyl)-4-hydroxy-piperidin-1-yl]-acetamide

EXAMPLE 26

2-[4-Hydroxy-4-(4-methyl-benzyl)-piperidin-1-yl]-N-(4-hydroxy-phenyl)-propionamide hydrochloride The title compound, m.p. 257° C. and MS: m/e=369.3 $(M+H^+)$, was prepared from N-[4-(tert-Butyl-dimethyl-silanyloxy)-phenyl]-2-[4-hydroxy-4-(4-methyl-benzyl)-piperidin-1-yl]-propionamide

EXAMPLE 27

3-(4-Benzyl-4-hydroxy-piperidin-1-yl)-N-(4-hydroxy-phenyl)-propionamide hydrochloride The title compound, m.p. 140°–145° C. and MS: m/e=355.4 $(M+H^+)$, was prepared from 3-(4-Benzyl-4-hydroxy-piperidin-1-yl)-N-[4-(tert-butyl-dimethyl-silanyloxy)-phenyl]-propionamide

EXAMPLE 28

4-Benzyl-1-[2-(4-hydroxy-phenylamino)-ethyl]-piperidin-4-ol hydrochloride

A solution of 2-(4-Benzyl-4-hydroxy-piperidin-1-yl)-N-[4-(tert-butyl-dimethyl-silanyloxy)-phenyl]-acetamide (0.97 g, 2.13 mmol) in THF (5 ml) was added dropwise to a room temperature suspension of $LiAlH_4$ (0.162 g, 4.26 mmol) in THF (5 ml). After 20 hours at room temperature, the reaction mixture was refluxed during 3 hours. The reaction mixture was cooled to 0° C., and treated successively with $H_2O$ (0.2 ml), 5N NaOH (0.2 ml) and H₂O (0.6 ml). After evaporation of THF, the resulting solid was filtered and washed with CH₂Cl₂. The aqueous phase was extracted with CH₂Cl₂ (3×10 ml), the combined organic phases were dried over Na₂SO₄ and concentrated. The residue was dissolved with CH₂Cl₂ (5ml) and stirred in the presence of tetra-n-butylammonium fluoride/SiO₂ (0.5 g, 0.55 mmol, 1.1 mmol/g). After 4 hours at room temperature, the reaction mixture was quenched with 20% NH₄Cl (15 ml) and the aqueous phase was extracted with CH₂Cl₂ (2×5ml). Combined organic phases were dried over Na₂SO₄ and concentrated. The residue was chromatographed over silica gel (CH₂Cl₂—MeOH 9:1 then 4:1) to give a foam which was dissolved in MeOH and treated with 1N HCl (0.6 ml). The solution was concentrated and the residue was dissolved with ethanol (EtOH). Addition of ether provided 4-Benzyl-1-[2-(4-hydroxy-phenylamino)-ethyl]-piperidin-4-ol hydrochloride (0.045 g, 5.3%) as beige solid, m.p. 130°–140° C. and MS: m/e=327.4 (M+H⁺).

EXAMPLE 29

4-Benzyl-1-[3-(4-hydroxy-phenylamino)-propyl]-piperidin-4-ol hydrochloride

A solution of 3-(4-Benzyl-4-hydroxy-piperidin-1-yl)-N-[4-(tert-butyl-dimethyl-silanyloxy)-phenyl]-propionamide (0.71 g, 1.51 mmol) in THF (4 ml) was added dropwise to a 0° C. suspension of LiAlH₄ (0.115 g, 3.02 mmol) in THF (4 ml). The reaction mixture was refluxed during 30 min, cooled to 0° C. and quenched carefully with H₂O (5 ml). After dilution with H₂O (20 ml), the reaction mixture was treated successively with 2N HCl and sat. NaHCO₃. The aqueous phase was extracted with CH₂Cl₂ (3×10 ml), the combined organic phases were dried over Na₂SO₄ and concentrated. The residue was chromatographed over silica gel (CH₂Cl₂—MeOH 9:1 then 4:1) to give a foam which was dissolved in MeOH and treated with excess HCl/ether. The solution was concentrated and the residue was dissolved with EtOH. Addition of ether provided 4-Benzyl-1-[3-(4-hydroxy-phenylamino)-propyl]-piperidin-4-ol hydrochloride (0.160 g, 26%) as beige solid, m.p. 213°–216° C. and MS: m/e=341.5 (M+H⁺).

EXAMPLE 30

(RS)-4-Benzyl-1-[2-hydroxy-3-(4-hydroxy-phenyl)-propyl]-piperidin-4-ol hydrochloride (RS)-4-Oxiranylmethyl-phenol (0.12 g, 0.8 mmol) was dissolved in MeOH (3 ml) and refluxed for 3 hours in the presence of 4-Benzyl-4-hydroxy-piperidin (0.19 g, 1.0 mmol). Reaction mixture was concentrated and the residue was chromatographed over silica gel (CH₂Cl₂—MeOH 19:1 then 9:1 then 4: 1) to give a white foam which was dissolved in MeOH (3 ml) and treated with 1N HCl (0.5 ml). The solution was concentrated and the residue was dissolved in MeOH (2 ml). Addition of ether provided (RS)-4-Benzyl-1-[2-hydroxy-3-(4-hydroxy-phenyl)-propyl]-piperidin-4-ol hydrochloride (0.112 g, 37%) as white solid mixture of the E/Z isomers, m.p. 135°–136° C. and MS: m/e=341 (M⁺).

Following the general method of Example 30 the compounds of Example 31 to Example 32 were prepared.

EXAMPLE 31

(RS)-1-[2-Hydroxy-3-(4-hydroxy-phenyl)-propyl]-4-(4-methyl-benzyl )-piperidin-4-ol hydrochloride The title compound, m.p. 196°–197° C. and MS: m/e=355 (M⁺), was prepared from (RS)-4-Oxiranylmethyl-phenol and 4-(4-Methyl-benzyl)-piperidin-4-ol.

EXAMPLE 32

(RS)-4-(4-Chloro-benzyl)-1-[2-hydroxy-3-(4-hydroxy-phenyl)-propyl]-piperidin-4-ol hydrochloride The title compound, m.p. 172°–174° C. and MS: m/e= 376.4 (M+H⁺), was prepared from (RS)-4-Oxiranylmethyl-phenol and 4-(4-Chloro-benzyl)-piperidin-4-ol.

EXAMPLE 33

1-(4-Benzyl-4-hydroxy-piperidin-1-yl)-3-(4-hydroxy-phenyl)-propan-2-one hydrochloride 1-(4-Benzyl-4-hydroxy-piperidin-1-yl)-3-[4-(tert-butyl-dimethyl-silanyloxy)-phenyl]-propan-2-one (0.400 g, 0.88 mmol) was dissolved in THF (4 ml) and stirred for 16 hours at room temperature in the presence of 1N tetra-n-butylammonium fluoride (1 ml, 1 mmol). The reaction mixture was quenched with 20% NH₄Cl (15 ml) and the aqueous phase was extracted with ethyl acetate (3×20 ml). Combined organic phases were dried over Na₂SO₄ and concentrated. The residue was chromatographed over silica gel (ethyl acetate) to give a yellow oil which was dissolved in MeOH (2 ml) and treated with 1N HCl (0.5 ml). The solution was concentrated, the residue was dissolved in isopropanol (i-PrOH) and ether was added to provide 1-(4-Benzyl-4-hydroxy-piperidin-1-yl)-3-(4-hydroxy-phenyl)-propan-2-one hydrochloride (0.120 g, 36%) as white solid, m.p. 180°–181° C. and MS: m/e=340.3 (M+H⁺).

EXAMPLE 34

4-Hydroxy-benzoic acid 2-[4-hydroxy-4-(4-methyl-benzyl)-piperidin-1-yl]ethylester hydrochloride (1:1)

4-Benzyloxy-benzoic acid 2-[4-hydroxy-4-(4-methyl-benzyl)-piperidin-1-yl]-ethyl ester (0.63 g, 1.37 mmol) was dissolved in THF (12 ml) and refluxed 8 hours in the presence of Pd/C (10%) (31 mg) under an atmospheric pressure of hydrogen. After filtration of the catalyst and evaporation of the solvent, the residue was crystallized in the presence of ethylacetate (15 ml). The white solid was dissolved in THF (10 ml) and a saturated solution of HCl in ether was added to provide 4-hydroxy-benzoic acid 2-[4-hydroxy-4-(4-methyl-benzyl)-piperidin-1-yl]ethylester hydrochloride (0.2 g, 37%) as a colorless solid mixture of the E/Z isomers, m.p. 151°–152° C. and MS: m/e=370.3 (M+H⁺).

Following the general method of Example 34, the compound of Example 35 was prepared.

EXAMPLE 35

4-Hydroxy-benzoic acid 3-[4-hydroxy-4-(4-methyl-benzyl)-piperidin-1-yl]-propylester hydrochloride (1:1)

The title compound, m.p. 178°–179° C. and MS: m/e= 384.3 (M+H⁺) was prepared from 4-benzyloxy-benzoic acid 3-[4-hydroxy-4-(4-methyl-benzyl)-piperidin-1-yl]-propyl ester.

EXAMPLE 36

N-[2-(4-Benzyl-4-hydroxy-piperidin-1-yl)-ethyl]-4-hydroxy-benzamide

Palladium on carbon (10%, 150 mg) was added to a solution of 4-benzyloxy-N-[2-(4-hydroxy-4-phenylpiperidin-1-yl]-ethyl]-benzamide (500 mg, 1.12 mmol) in acetic acid (20 ml). The hydrogenation was complete after 3 h. The catalyst was removed by filtration through celite and the solvent was evaporated. Addition of sodium bicarbonate (10% aq. solution, 2 ml) and extraction with dichloromethane afforded N-[2-(4-benzyl-4-hydroxy-piperidin-1-yl)-ethyl]-4-hydroxy-benzamide (399 mg, 95%) as a light yellow solid.

EXAMPLE 37

4-Hydroxy-N-[2-[4-hydroxy-4-(4-methyl-benzyl)-piperidin-1-yl]-ethyl]-benzamide hydrochloride (1:1)

Palladium on carbon (10%, 145 mg) was added to a solution of 4-benzyloxy-N-[2-[4-hydroxy-4-(4-methyl-benzyl)-piperidin-1-yl]-ethyl]-benzamide (780 mg, 1.7 mmol) in acetic acid (20 ml). The hydrogenation was complete after 4 h. The catalyst was removed by filtration through celite and the solvent was evaporated. Sodium bicarbonate (10% aq. solution, 2 ml) was added, and the aqueous layer extracted with dichloromethane. The organic layer was dried ($Na_2SO_4$), filtered and evaporated. The residue was dissolved in dichloromethane (3 ml) and saturated HCl in ether was added. The precipitate was filtered to give 4-benzyloxy-N-[2-[4-hydroxy-4-(4-methyl-benzyl)-piperidin-1-yl]-ethyl]-benzamide hydrochloride (1:1) (460 mg, 67%) as a white solid. MS: me/e=369 $(M+H)^+$.

EXAMPLE 38

N-[3-(4-Benzyl-4-hydroxy-piperidin-1-yl)-propyl]-4-hydroxy-benzamide

Palladium on carbon (10%, 50 mg) was added to a solution of N-[3-(4-benzyl-4-hydroxy-piperidin-1-yl)-propyl]-4-benzyloxy-benzamide (185 mg, 0.40 mmol) in acetic acid (5 ml). The hydrogenation was complete after 4 h. The catalyst was removed by filtration through celite and the solvent was evaporated. Sodium bicarbonate (10% aq. solution, 2 ml) was added, and the aqeous layer extracted with dichloromethane. The organic layer was dried ($Na_2SO_4$), filtered and evaporated to give N-[3-(4-benzyl-4-hydroxy-piperidin-1-yl)-propyl]-4-hydroxy-benzamide (130 mg, 87%) as a white solid. MS: me/e=369 $(M+H)^+$.

EXAMPLE 39

4-Hydroxy-N-[3-[4-hydroxy-4-(4-methyl-benzyl)-piperidin-1-yl]-propyl]-benzamide

Palladium on carbon (10%, 50 mg) was added to a solution of 4-benzyloxy-N-[3-[4-hydroxy-4-(4-methyl-benzyl)-piperidin-1-yl]-propyl]-benzamide (220 mg, 0.46 mmol) in acetic acid (5 ml). The hydrogenation was complete after 4 h. The catalyst was removed by filtration through celite and the solvent was evaporated. Sodium bicarbonate (10% aq. solution, 2 ml) was added, and the aqeous layer extracted with dichloromethane. The organic layer was dried ($Na_2SO_4$), filtered and evaporated to give 4-hydroxy-N-[3-[4-hydroxy-4-(4-methyl-benzyl)-piperidin-1-yl]-propyl]-benzamide (178 mg,73%) as a white solid. MS: me/e=383 $(M+H)^+$.

EXAMPLE 40

4-Hydroxy-N-[2-[4-hydroxy-4-(4-methyl-benzyl)-piperidin-1-yl]-ethyl]-N-methyl-benzamide Palladium on carbon (10%, 60 mg) was added to a solution of 4-benzyloxy-N-[2-[4-hydroxy-4-(4-methyl-benzyl)-piperidin-1-yl]-ethyl]-N-methyl-benzamide (226 mg, 0.48 mmol) in acetic acid (6 ml). The hydrogenation was complete after 4 h. The catalyst was removed by filtration through celite and the solvent was evaporated. Sodium bicarbonate (10% aq. solution, 2 ml) was added, and the aqeous layer extracted with dichloromethane. The organic layer was dried ($Na_2SO_4$), filtered and to give 4-hydroxy-N-[2-[4-hydroxy-4-(4-methyl-benzyl)-piperidin-1-yl]-ethyl ]-N-methyl-benzamide (135 mg, 74%) as a white solid. MS: me/e=383 $(M+H)^+$.

EXAMPLE 41

(E)-1-[3-(4-Hydroxy-phenyl)-allyl]-4-(4-methyl-benzyl)-piperidin-4-ol

To a suspension of lithium aluminium hydride (324 mg, 3.0 eq.) and THF (50 ml) at r.t under argon, a solution of (E)-1-[4-hydroxy-4-(4-methyl-benzyl)-piperidin-1-yl]-3-( 4-hydroxy-phenyl)-propenone (1.0 g, 2.85 mmol) in THF (10 ml) is slowly added. After stirring for 5 h., a 20% ammonium chloride solution (20 ml) is carefully added, and the aqeous layer is extracted with dichloromethane. The organic layer is dried ($Na_2SO_4$), filtered and evaporated. The oily residue is purified by chromatography (Silica gel, dichloromethane-methanol-25% aqeous ammonia 140:10:1) to give (E)-1-[3-(4-hydroxy-phenyl)-allyl]-4-(4-methyl-benzyl)-piperidin-4-ol (474 mg, 49%) as a white foam. MS: me/e=338 $(M+H)^+$.

Synthesis of intermediates

EXAMPLE 42

4-Hydroxy-4-(4-methyl-benzyl)-piperidin-1-carboxylic acid ethylester

A solution of 1-ethoxycarbonyl-4-piperidone (39 ml, 0.26 mol) in diethylether (150 ml) was added dropwise at room temperature to a solution prepared from 4-methyl-benzylbromide (237 g, 1.28 mol) and Mg (31.2 g, 1.28 mol) in diethylether (300 ml). Room temperature was maintained for 45 min with stirring and the mixture was then refluxed for 5 h. It was cooled to 0° C., diluted with diethylether (700 ml) and hydrolyzed with saturated ammoniumhydrochloride solution (200 ml) and water (350 ml). Insoluble material was removed by filtration over Celite", the residue washed twice with diethylether (2×500 ml) and the organic phase was separated. The water layer was extracted with diethylether, the organic phases were pooled and dried with $MgSO_4$ and the solvent evaporated. The residue was chromatographed over silica gel (hexane-ethyl acetate, 2:1) to give 4-hydroxy-4-(4-methyl-benzyl)-piperidin-1-carboxylic acid ethylester (70.5 g, 99%) as a yellowish oil, MS: m/e=278 $(M+H^+)$.

Following the general method of Example 42, the compound of Example 43 was prepared.

EXAMPLE 43

4-(4-Fluoro-benzyl)-4-hydroxy-piperidin-1-carboxylic acid ethylester

The title compound was prepared from 1-ethoxycarbonyl-4-piperidone and 4-fluoro-benzylbromide.

EXAMPLE 44

4-(4-Methyl-benzyl)-piperidin-4-ol

A mixture of 4-hydroxy-4-(4-methyl-benzyl)-piperidin-1-carboxylic acid ethylester (70.5 g, 0.25 mol) and sodium hydroxide (26 g, 0.65 mol) in ethanol (350 ml) and water (50 ml) was refluxed for 2 days. Sodium hydroxide (20 g, 0.50 mol) was added and refluxing commenced for another day before cooling to room temperature and evaporating the solvent. The residue was taken up with $CH_2Cl_2$ (700 ml) and water (1 l), the organic phase was separated and the water phase extracted with $CH_2Cl_2$. The organic phases were pooled, dried with $MgSO_4$ and the solvent was evaporated. The residue was crystallized from n-hexane to give 4-(4-methyl-benzyl)-piperidin-4-ol (34 g, 66%) as an off-white solid, m.p. 118°–121° C. and MS: m/e=206 ($M^+$).

Following the general method of Example 44, the compounds of Example 45 to Example 46 were prepared.

EXAMPLE 45

4-(4-Fluoro-benzyl)-piperidin-4-ol

The title compound was prepared from 4-(4-fluoro-benzyl)-4-hydroxy-piperidin-1-carboxylic acid ethylester.

EXAMPLE 46

4-(4-Methoxy-benzyl)-piperidin-4-ol

The title compound was prepared from 4-(4-methoxy-benzyl)-4-hydroxy-piperidin-1-carboxylic acid ethylester.

EXAMPLE 47

(R)-{[4-(Phenylmethoxy)phenoxy]methyl}-oxirane

A mixture of hydroquinone monobenzylether (1.7 g, 8.5 mmol) and tetramethylammoniumchloride (0.19 g, 1.7 mmol) in (S)-epichlorohydrine (2.0 ml, 25.5 mmol) was stirred at room temperature for 4 days. $H_2O$ (30 ml) and $CH_2Cl_2$ (50 ml) were added and the organic phase was separated. The water phase was extracted two times with $CH_2Cl_2$. The organic phases were then pooled, dried with $Na_2SO_4$ and the solvent evaporated. The residue was chromatographed over silica gel (hexane-$Et_2O$, 3:1) to give (R)-{[4-(Phenylmethoxy)phenoxy]methyl}-oxirane (1.1 g, 50%) as a colorless solid, m.p. 70°–73° C., $[\alpha]_D^{20}$=–8.1° (c=1.0, methanol) and MS: m/e=256 ($M^+$).

EXAMPLE 48

(RS)-1-[3-(4-Benzyloxy-phenoxy)-2-hydroxy-propyl]-4-(4-methyl-benzyl)-piperidin-4-ol A mixture of (RS)-1-chloro-3-[4-(benzyloxy)phenoxy]-2-propanol (1.0 g, 3.4 mmol), 4-(4-methyl-benzyl)-piperidin-4-ol (0.70 g, 3.4 mmol) and potassium carbonate (0.50 g, 3.6 mmol) in 2-butanone was refluxed for 2 days. It was cooled to room temperature, 50 ml of $H_2O$ were added and the organic phase was separated. The water phase was extracted two times with ethyl acetate. The organic phases were then pooled, dried with $Na_2SO_4$ and the solvent evaporated. The residue was chromatographed over silica gel ($CH_2Cl_2$—MeOH, 98:2) to give (RS)-1-[3-(4-benzyloxy-phenoxy)-2-hydroxy-propyl]-4-(4-methyl-benzyl)-piperidin-4-ol as a colorless solid (0.75 g, 48%). MS: m/e=462.5 ($M+H^+$)

Following the general method in Example 48 the intermediates of Example 49 to Example 50 were prepared.

EXAMPLE 49

(RS)-4-Benzyl-1-[3-(4-benzyloxy-phenoxy)-2-hydroxy-propyl]-piperidin-4-ol

The title compound was prepared from (RS)-1-chloro-3-[4-(benzyloxy)phenoxy]-2-propanol and 4-benzyl-4-hydroxy-piperidine.

EXAMPLE 50

(RS)-1-[3-(4-Benzyloxy-phenoxy)-2-hydroxy-propyl]-4-(4-fluoro-benzyl)-piperidin-4-ol The title compound, MS: m/e=466.5 ($M+H^+$), was prepared from (RS)-1-chloro-3-[4-(benzyloxy)phenoxy]-2-propanol and 4-(4-Fluoro-benzyl)-piperidin-4-ol (Example 37).

EXAMPLE 51

(R)-4-Benzyl-1-[3-(4-benzyloxy-phenoxy)-2-hydroxy-propyl]-piperidin-4-ol (R)-{[4-(Phenylmethoxy)phenoxy]methyl}-oxirane (0.55 g, 2.2 mmol) and 4-benzyl-4-hydroxy-piperidine (0.49 g, 2.4 mmol) were dissolved in ethanol (10 ml) and refluxed for 2 h. After evaporation of the solvent, the residue was chromatographed over silica gel (ethyl acetate-MeOH, 9:1) to give (R)-4-benzyl-1-[3-(4-benzyloxy-phenoxy)-2-hydroxy-propyl]-piperidin-4-ol (0.85 g, 88%) as colorless oil. MS: m/e=448.5 ($M+H^+$).

EXAMPLE 52

(S)-4-Benzyl-1-[3-(4-benzyloxy-phenoxy)-2-hydroxy-propyl]-piperidin-4-ol (S)-{[4-(Phenylmethoxy)phenoxy]methyl}-oxirane (0.55 g, 2.2 mmol) and 4-benzyl-4-hydroxy-piperidine (0.49 g, 2.4 mmol) were dissolved in ethanol (10 ml) and refluxed for 2h. After evaporation of the solvent, the residue was chromatographed over silica gel (ethyl acetate-MeOH, 9:1) to give (S)-4-benzyl-1-[3-(4-benzyloxy-phenoxy)-2-hydroxy-propyl]-piperidin-4-ol (0.89 g, 92%) as colorless oil. MS: m/e =448.5 ($M+H^+$).

EXAMPLE 53

(RS)-1-[3-(4-Amino-phenoxy)-2-hydroxy-propyl]-4-benzyl-piperidin-4-ol hydrochloride (RS)-4-Benzyl-1-[2-hydroxy-3-(4-nitro-phenoxy)-propyl]-piperidin-4-ol hydrochloride (3.0 g, 7.1 mmol) was dissolved in a mixture of ethanol (250 ml) and MeOH (80 ml) and hydrogenated in the presence of Pd on C at room temperature and atmospheric pressure. After filtration and evaporation of the solvent, the residue was dissolved in ethanol (20 ml) and ethyl acetate (40 ml) to give (RS)-1-[3-(4-amino-phenoxy)- 2-hydroxy-propyl]-4-benzyl-piperidin-4-ol hydrochloride (2.5 g, 90%) as beige solid mixture of the E/Z isomers, m.p. 93°–95° C. and MS: m/e=357.4 ($M+H^+$)

EXAMPLE 54

4-Benzyl-1-(3-chloro-2-hydroxy-propyl)-piperidin-4-ol (rac)-Epichlorohydrin (2.5 ml, 31 mmol) dissolved in diethylether (10 ml) was added at room temperature to a suspension of 4-benzyl-4-hydroxy-piperidine (6.0 g, 31 mmol) in diethylether (40 ml) and $CH_2Cl_2$ (40 ml). The mixture was stirred overnight at room temperature, water (50 ml) and $CH_2Cl_2$ (50 ml) were added and the organic phase was separated. The water phase was extracted with $CH_2Cl_2$, the organic phases were pooled, dried with $Na_2SO_4$ and the solvents evaporated. The residue was chromatographed over silica gel (ethyl acetate-MeOH, 9:1) to give 4-benzyl-1-(3-chloro-2-hydroxy-propyl)-piperidin-4-ol (1.0 g, 13%) as a colorless solid, m.p. 194°–195° C. and MS: m/e=(M+H$^+$).

EXAMPLE 55

4-Benzyl-1-[2-(4-benzyloxy-phenoxy)-ethyl]-piperidin-4-ol

A mixture of 4-benzyl-4-hydroxy-piperidine (0.62 g, 3.3 mmol), 1-(2-bromoethoxy)-4-(phenylmethoxy)-benzene (1.0 g, 3.3 mmol) and potassium carbonate (0.9 g, 6.5 mmol) in 2-butanone (15 ml) was refluxed overnight. It was cooled to room temperature, 30 ml of H$_2$O were added and the organic phase was separated. The water phase was extracted two times with ethyl acetate. The organic phases were then pooled, dried with Na$_2$SO$_4$ and the solvent evaporated to give 4-benzyl-1-[2-(4-benzyloxy-phenoxy)-ethyl]-piperidin-4-ol as a yellowish solid (1.35 g, 99%). MS: m/e=418.4 (M+H$^+$).

Following the general method of Example 55, the compounds of Example 56 to Example 63 were prepared.

EXAMPLE 56

1-[2-(4-Benzyloxy-phenoxy)-ethyl]-4-(4-methyl-benzyl)-piperidin-4-ol

The title compound, MS: m/e=432.6 (M+H$^+$), was prepared from 1-(2-bromoethoxy)-4-(benzyloxy)-benzene and 4-(4-methyl-benzyl)-piperidin-4-ol.

EXAMPLE 57

1-[2-(4-Benzyloxy-phenoxy)-ethyl]-4-(4-fluor-benzyl)-piperidin-4-ol

The title compound, MS: m/e=436.5 (M+H$^+$), was prepared from 1-(2-bromoethoxy)-4-(benzyloxy)-benzene and 4-(4-fluoro-benzyl)-piperidin-4-ol.

EXAMPLE 58

4-Benzyl-1-[3-(4-benzyloxy-phenoxy)-propyl]-piperidin-4-ol

The title compound, MS: m/e=432.6 (M+H$^+$), was prepared from 1-(2-bromopropoxy)-4-(benzyloxy)-benzene and 4-benzyl-piperidin-4-ol.

EXAMPLE 59

1-[3-(4-benzyloxy-phenoxy)-propyl]-4-(4-fluoro-benzyl)-piperidin-4-ol.

The title compound, MS: m/e=450.5 (M+H$^+$), was prepared from 1-(3-bromopropoxy)-4-(benzyloxy)-benzene and 4-(4-fluor-benzyl)-piperidin-4-ol.

EXAMPLE 60

1-[3-(3-benzyloxy-phenoxy)-propyl]-4-(4-methyl-benzyl)-piperidin-4-ol.

The title compound, MS: m/e=446.5(M+H$^+$), was prepared from 1-(3-bromopropoxy)-3-(phenylmethoxy)-benzene and 4-(4-methyl-benzyl)-piperidin-4-ol.

EXAMPLE 61

1-[3-(2-benzyloxy-phenoxy)-propyl]-4-(4-methyl-benzyl)-piperidin-4-ol.

The title compound, MS: m/e=446.5(M+H$^+$), was prepared from 1-(3-bromopropoxy)-2-(benzyloxy)-benzene and 4-(4-methyl-benzyl)-piperidin-4-ol.

EXAMPLE 62

1-[2-(4-benzyloxy-phenoxy)-ethyl]-4-(4-methoxy-benzyl)-piperidin-4-ol

The title compound, MS: m/e=448.5 (M+H$^+$), was prepared from 1-(2-bromoethoxy)-4-(benzyloxy)-benzene and 4-(4-methoxy-benzyl)-piperidin-4-ol.

EXAMPLE 63

1-[2-(4-benzyloxy-phenoxy)-ethyl]-4-(4-methoxy-benzyl)-piperidin-4-ol

The title compound, MS: m/e=446.4 (M+H$^+$), was prepared from methanesulfonic acid 2-[4-hydroxy-4-(4-methyl-benzyl)-piperidin-1-yl]-1-methyl ethyl ester and 4-benzyloxy-phenol.

EXAMPLE 64

2-(4-Benzyl-4-hydroxy-piperidin-1-yl)-N-[4-(tert-butyl-dimethyl-silanyloxy)-phenyl]-acetamide N-[4-(tert-Butyl-dimethyl-silanyloxy)-phenyl]-2-chloro-acetamide (1.14 g, 3.8 mmol) was dissolved in dimethyl-formamide (DMF) (12 ml) and stirred for 19 hours at room temperature in the presence of triethylamine (0.79 ml, 5.7 mmol) and 4-benzyl-4-hydroxypiperidin (0.87 g, 4.56 mmol). The reaction mixture was concentrated, dissolved in CH$_2$Cl$_2$ and washed with H$_2$O (2×30 ml). The organic phase was dried over Na$_2$SO$_4$ and concentrated. The residue was chromatographed over silica gel (hexane-ethyl acetate 1:1 then ethyl acetate) to provide 2-(4-Benzyl-4-hydroxy-piperidin-1-yl)-N-[4-(tert-butyl-dimethyl-silanyloxy)-phenyl]-acetamide (1.32 g, 78%) as a yellow solid, m.p. 105°–108° C. and MS: m/e=455.5 (M+H$^+$).

Following the general method of Example 64, the compounds of Example 65 to Example 68 were prepared.

EXAMPLE 65

N-[4-(tert-Butyl-dimethyl-silanyloxy )-phenyl]-2-[4-hydroxy-4-(4-methyl-benzyl)-piperidin-1-yl]-acetamide The title compound, m.p. 136°–138° C. and MS: m/e=468 (M$^+$), was prepared from N-[4-(tert-Butyl-dimethyl-silanyloxy)-phenyl]-2-chloro-acetamide and 4-(4-Methyl-benzyl)-piperidin-4-ol.

EXAMPLE 66

N-[4-(tert-Butyl-dimethyl-silanyloxy)-phenyl]-2-[4-(4-chloro-benzyl)-4-hydroxy-piperidin-1-yl]-acetamide The title compound, m.p. 135°–136° C. and MS: m/e= 489.4 (M$^+$), was prepared from N-[4-(tert-Butyl-dimethyl-silanyloxy)-phenyl]-2-chloro-acetamide and 4-(4-Chloro-benzyl)-piperidin-4-ol.

EXAMPLE 67

(RS)-N-[4-(tert-Butyl-dimethyl-silanyloxy)-phenyl]-2-[4-hydroxy-4-(4-methyl-benzyl)-piperidin-1-yl]-propionamide The title compound, m.p. 134°–138° C. and MS: m/e= 483.3 (M+H$^+$), was prepared from (RS)-N-[4-tert-Butyl-dimethyl-silanyloxy)-phenyl]-2-chloro-propionamide and 4-(4-Methyl-benzyl)-piperidin-4-ol.

EXAMPLE 68

3-(4-Benzyl-4-hydroxy-piperidin-1-yl)-N-[4-(tert-butyl-dimethyl-silanyloxy)-phenyl]-propionamide The title compound, MS: m/e=468 (M$^+$), was prepared from N-[4-(tert-Butyl-dimethyl-silanyloxy)-phenyl]-3-chloro-propionamide and 4-benzyl-4-hydroxypiperidin.

EXAMPLE 69

N-[4-(tert-Butyl-dimethyl-silanyloxy)-phenyl]-2-chloro-acetamide 4-(tert-Butyl-dimethyl-silanyloxy)-phenylamine (2.23 g, 10 mmol) was dissolved in acetone (25 ml). After addition of Na$_2$CO$_3$ (3.2 g, 30 mmol), chloroacetylchloride (0.96 ml, 12 mmol) was added dropwise. After 1 hour at room temperature, the reaction mixture was quenched with H$_2$O (100 ml) and the aqueous phase was extracted with CH$_2$Cl$_2$ (3×10 ml). Combined organic phases were dried over Na$_2$SO$_4$ and concentrated. The residue was chromatographed over silica gel (hexane-ethyl acetate 9:1 then hexane-ethyl acetate 4:1) to provide N-[4-(tert-Butyl-dimethyl-silanyloxy)-phenyl]-2-chloro-acetamide (2.55 g, 71%) as a colorless solid, m.p. 107°–108° C. and MS: m/e=299 (M$^+$).

Following the general method of Example 69, the compounds of Example 70 to Example 71 were prepared.

EXAMPLE 70

(RS)-N-[4-tert-Butyl-dimethyl-silanyloxy)-phenyl]-2-chloro-propionamide

The title compound, m.p. 74°–75° C. and MS: m/e=313 (M$^+$), was prepared from 4-(tert-Butyl-dimethyl-silanyloxy)-phenylamine and (RS)-2-chloropropionyl chloride.

EXAMPLE 71

N-[4-(tert-Butyl-dimethyl-silanyloxy)-phenyl]-3-chloro-propionamide

The title compound, m.p. 126° C. and MS: m/e=313 (M$^+$), was prepared from 4-(tert-Butyl-dimethyl-silanyloxy)-phenylamine and 3-chloropropionyl chloride.

EXAMPLE 72

4-(tert-Butyl-dimethyl-silanyloxy)-phenylamine tert-Butyl-dimethyl-(4-nitro-phenoxy)-silane (7.3 g, 2.9 mmol) was dissolved in MeOH (75 ml) and hydrogenated in the presence of Pd on C (10%, E 101 N/D) at room temperature and atmospheric pressure for 1 hour. The catalyst was filtered and the solvent was evaporated to provide 4-(tert-Butyl-dimethyl-silanyloxy)-phenylamine (6.4 g, 99%) as light yellow oil, MS: m/e=223 (M$^+$).

EXAMPLE 73 tert-Butyl-dimethyl-(4-nitro-phenoxy)-silane

4-Nitrophenol (5.6 g, 40 mmol) was dissolved in CH$_2$Cl$_2$ (200 ml) and stirred at room temperature in the presence of tertbutyldimethyl-silyl chloride (7.8 g, 52 mmol), 4-dimethylaminopyridine (0.1 g, 0.8 mmol) and triethylamine (7.2 ml, 52 mmol). After 30 minutes at room temperature, the reaction mixture was washed with H$_2$O (2×200 ml) and the resulting aqueous phases were extracted with CH$_2$Cl$_2$ (100 ml). The combined organic phases were dried over Na$_2$SO$_4$ and concentrated. The residue was chromatographed over silica gel (hexane-ether 9:1) to provide tert-Butyl-dimethyl-(4-nitro-phenoxy)-silane (10 g, 100%) as a yellow solid, m.p. 36°–38° C. and MS: m/e=253 (M$^+$).

EXAMPLE 74

1-(4-Benzyl-4-hydroxy-piperidin-1-yl)-3-[4-(tert-butyl-dimethyl-silanyloxy)-phenyl]-propan-2-one To a solution of oxalylchloride (0.28 ml, 3.3 mmol) in CH$_2$Cl$_2$ (4 ml) at −78° C. was added dropwise dimethyl sulfoxide (DMSO) (0.47 ml, 6.6 mmol). After 30 min., a solution of (RS)-4-Benzyl-1-{3-[4-(tert-butyl-dimethyl-silanyloxy)-phenyl]-2-hydroxy-propyl}-piperidin-4-ol (0.75 g, 1.65 mmol) in CH$_2$Cl$_2$ (4 ml) was added. After another hour at −78° C., triethylamine (1.8 ml, 13.2 mmol) was added and reaction mixture was allowed to warm up slowly to room temperature. After 1 hour, 20% NH$_4$Cl (15 ml) was added, the resulting aqueous phase was extracted with CH$_2$Cl$_2$ (3×30 ml). Combined organic phases were dried over Na$_2$SO$_4$ and concentrated. The residue was chromatographed over silica gel (hexane-ethylacetate 1:1 then ethyl acetate) to provide 1-(4-Benzyl-4-hydroxy-piperidin-1-yl)-3-[4-(tert-butyl-dimethyl-silanyloxy)-phenyl]-propan-2-one (0.4 g, 54%) as a yellow oil, and MS: m/e=454.5 (M+H$^+$).

EXAMPLE 75

(RS)-4-Benzyl-1-{3-[4-(tert-butyl-dimethyl-silanyloxy)-phenyl]-2-hydroxy-propyl}-piperidin-4-ol (RS)-tert-Butyl-dimethyl-(4-oxiranylmethyl-phenoxy)-silane (0.62 g, 2.34 mmol) was dissolved in MeOH (8 ml) and stirred overnight at room temperature in the presence of 4-benzyl-4-hydroxy-piperidine (0.9 g, 4.68 mmol). The reaction mixture was concentrated and the residue was chromatographed over silica gel (hexane-ethylacetate 1:1, then CH$_2$Cl$_2$—MeOH 19:1) to provide (RS)-4-Benzyl-1-{3-[4-(tert-butyl-dimethyl-silanyloxy)-phenyl]-2-hydroxy-propyl}-piperidin-4-ol (0.95 g, 90%) as a yellow oil, MS: m/e=456.5 (M+H$^+$).

EXAMPLE 76

(RS)-tert-Butyl-dimethyl-(4-oxiranylmethyl-phenoxy)-silane (RS)-4-Oxiranylmethyl-phenol (1 g, 6.66 mmol) was dissolved in CH$_2$Cl$_2$ (50 ml) and stirred at room temperature in the presence of tert-butyldimethylsilyl chloride (1.3 g, 8.66 mmol), 4-dimethyl-aminopyridine (0.018 g, 0.15 mmol) and triethylamine (1.2 ml, 8.66 mmol). After 22 hours at room temperature, the reaction mixture was washed with H$_2$O (2×100 ml) and the resulting aqueous phases were extracted with CH$_2$Cl$_2$ (100 ml). The combined organic phases were dried over Na$_2$SO$_4$ and concentrated. The residue was chromatographed over silica gel (hexane-ethylacetate 9:1) to provide (RS)-tert-Butyl-dimethyl-(4-oxiranylmethyl-phenoxy)-silane (1.44 g, 82%) as yellow oil, MS: m/e=264 (M$^+$).

EXAMPLE 77

(RS)-4-Oxiranylmethyl-phenol 4-allylphenol (8.9 g, 66.3 mmol) was dissolved in CH$_2$Cl$_2$ (180 ml). After addition of NaHCO$_3$ (8.4 g, 99.5 mmol), m-chloroperbenzoic acid 70% (18 g, 73 mmol) was added portionwise. After 6 hours at room temperature, additional NaHCO$_3$ (8.4 g, 99.5 mmol) and m-chloroperbenzoic acid 70% (18 g, 73 mmol) were added. After 17 hours, the reaction mixture was washed with sat. NaHCO$_3$ (200 ml) and the resulting aqueous phases were extracted with CH$_2$Cl$_2$ (3×10 ml). The combined organic phases were washed with sat. Na$_2$S$_2$O$_3$ (2×100 ml), dried over Na$_2$SO$_4$ and concentrated. The residue was chromatographed over silica gel (hexan-ethyl acetate 9:1 then 1:1) to provide (RS)-4-oxiranylmethyl-phenol (3.77 g, 38%) as yellow solid, m.p. 54°–57° C. and MS: m/e=150 (M$^+$).

EXAMPLE 78

4-allylphenol

To a −78° C. cold solution of 4-allylanisol (14.6 ml, 95 mmol) in CH$_2$Cl$_2$ (300 ml) BBr$_3$ (100 ml, 0.1 mol, 1 mol/l in CH$_2$Cl$_2$) was added dropwise. The reaction mixture was then allowed to warm up to room temperature. After 1 hour, the reaction mixture was cooled to 0° C. and quenched slowly with H$_2$O (90 ml). The resulting aqueous phase was extracted with CH$_2$Cl$_2$ (2×100 ml). The combined organic phases were dried over Na$_2$SO$_4$ and concentrated. The residue was chromatographed over silica gel (hexane-ethyl acetate 9:1) to provide 4-allylphenol (11.3 g, 89%) as a purple oil, MS: m/e=134 (M$^+$).

EXAMPLE 79

4-Benzyloxy-benzoic acid 2-[4-hydroxy-4-(4-methyl-benzyl)-piperidin-1-yl]-ethyl ester 4-Benzyloxybenzoic acid (0.685 g, 3 mmol) was dissolved in DMF (6 ml), and 1,1,-carbonyldiimidazole (0.58 g, 3.6 mmol) was added portionwise. The reaction mixture was heated to 55°–60° C. for 20 min. and then cooled to room temperature. A solution of 1-(2-hydroxy-ethyl)-4-(4-methyl-benzyl)-piperidin-4-ol (0.78 g, 3.3 mmol) in DMF (2 ml) was added. The reaction mixture was stirred 23 hours at room temperature and 4 hours at 60° C. H$_2$O (50 ml) was added followed by CH$_2$Cl$_2$. Organic phase was washed with sat. NaHCO$_3$, dried over Na$_2$SO$_4$, and concentrated. The residue was chromatographed over silica gel (CH$_2$Cl$_2$—MeOH, 19:1) to provide 4-benzyloxy-benzoic acid 2-[4-hydroxy-4-(4-methyl-benzyl)-piperidin-1-yl]-ethyl ester (0.65 g, 47%) as a colorless solid, m.p. 102° C. and MS: m/e=460.3 (M+H$^+$).

Following the general method of Example 79, the compound of Example 80 was prepared.

EXAMPLE 80

4-Benzyloxy-benzoic acid 3-[4-hydroxy-4-(4-methyl-benzyl)-piperidin-1-yl]-propyl ester The title compound, MS: m/e=474.4 (M+H$^+$) was prepared from 1-(3-hydroxy-propyl)-4-(4-methyl-benzyl)-piperidin-4-ol.

EXAMPLE 81

1-(2-Hydroxy-ethyl)-4-(4-methyl-benzyl)-piperidin-4-ol

A mixture containing 4-(4-methyl-benzyl)-piperidin-4-ol (5.1 g, 25 mmol), 2-bromoethanol (1.8 ml, 25 mmol) and K$_2$CO$_3$ (5.2 g, 37.5 mmol) in 2-butanone (120 ml) was refluxed for 22 hours. H$_2$O (30 ml) was added and the aqueous phase was extracted with ethylacetate. Combined organic phases were dried over Na$_2$SO$_4$, and concentrated. The residue was chromatographed over silica gel (CH$_2$Cl$_2$—MeOH, 9:1 +NH$_4$OH (1%)) to provide 1-(2-hydroxy-ethyl)-4-(4-methyl-benzyl)-piperidin-4-ol (4.3 g, 73%) as a yellow oil, MS: m/e=235.3 (M$^+$).

Following the general method of Example 81, the compound of Example 82 was prepared.

EXAMPLE 82

1-(3-Hydroxy-propyl)-4-(4-methyl-benzyl)-piperidin-4-ol

The title compound, MS: m/e=263.3 (M$^+$) was prepared from 4-(4-methyl-benzyl)-piperidin-4-ol and 3-bromo-1-propanol.

EXAMPLE 83

4-Benzyloxy-N-(2-hydroxy-ethyl)-benzamide

A solution of 4-benzyloxy benzoic acid (20 g, 87.6 mmol), 1,1,-carbonyl-diimidazole (14.9 g, 91.8 mmol) and DMF (80 ml) was stirred at 50° C. for 1 h. The solution is cooled to 0° C., and ethanolamine (25% in water, 81.2 g) is added. After 45 min., the precipitate was filtered to give 4-benzyloxy-N-(2-hydroxy-ethyl)-benzamide (22.49 g, 94.5%) as a white solid. MS: me/e=271 (M)$^+$.

EXAMPLE 84

4-Benzyloxy-N-(2-chloro-ethyl)-benzamide

Phosgene was bubbled through a suspension of 4-benzyloxy-N-(2-hydroxy-ethyl)-benzamide (22.49 g, 82.8 mmol) in dioxane (130 ml) until all the insoluble material had dissolved. Excess phosgene was removed by a stream of carbon dioxide. The solvent was removed at reduced pressure, and the residue was dried for 1 h. at 100° C. The crude product was recrystallized from ethyl acetate to yield 4-benzyloxy-N-(2-chloro-ethyl)-benzamide (16.3 g, 68%).

EXAMPLE 85

4-Benzyloxy-N-[2-(4-hydroxy-4-phenyl-piperidin-1-yl)-ethyl]-benzamide

A mixture of 4-benzyloxy-N-(2-chloro-ethyl)-benzamide (2.1 g, 7.25 mmol), 4-benzyl-4-hydroxy-piperidine (1.386 g, 7.25 mmol), potassium carbonate (2.0 g, 14.5 mmol) and 2-butanone (40 ml) was stirred for 15 h at 60° C. After the addition of water, the mixture was extracted with ethyl acetate. The organic layer was dried (Na$_2$SO$_4$), filtered and evaporated. The residue was purified by chromatography (silica gel, methylene chloride methanol from 95:5 to 9:1) to give 4-benzyloxy-N-[2-[4-hydroxy-4-(4-methyl-benzyl)-piperidin-1-yl]-ethyl]-benzamide (680 mg, 21%) as a light yellow solid. MS: me/e=445 (M+H)$^+$.

EXAMPLE 86

4-Benzyloxy-N-[2-[4-hydroxy-4-(4-methyl-benzyl)-piperidin-1-yl]-ethyl]-benzamide A mixture of 4-benzyloxy-N-(2-chloro-ethyl)-benzamide (2.0 g, 6.9 mmol), 4-hydroxy-4-(4-methyl-benzyl)-piperidine (1.06 g, 5.18 mmol), potassium carbonate (1.43 g, 10.35 mmol) and 2-butanone (40 ml) was stirred for 15 h at 60° C. After the addition of water, the mixture was extracted with ethyl acetate. The organic layer was dried (Na$_2$SO$_4$), filtered and evaporated. The residue was purified by chromatography (silica gel, methylene chloride methanol from 95:5 to 9:1) to give 4-benzyloxy-N-[2-[4-hydroxy-4-(4-methyl-benzyl)-piperidin-1-yl]-ethyl]-benzamide (445 mg, 19%) as a light yellow solid. MS: me/e =459 (M+H)$^+$.

EXAMPLE 87

4-Benzyloxy-N-(3-chloro-propyl)-benzamide

A mixture of 4-benzyloxy benzoic acid (5.0 g, 21.9 mmol), 1,1,-carbonyl-diimidazole (3.6 g, 1.05 eq.) and DMF (50 ml) was stirred at 50° C. for 1 h. After cooling to r.t., 3-chloropropylamine hydrochloride (3.4 g, 26.1 mmol) and sodium carbonate (3.5 g, 32.0 mmol) were added and stirring continued for 45 min. After the addition of water, the mixture was extracted with ether. The organic layer was dried (Na$_2$SO$_4$), filtered and evaporated to give 4-benzyloxy-N-(3-chloro-propyl)-benzamide (5.44 g, 85%) as a white solid. MS: me/e=304 (M+H)$^+$.

EXAMPLE 88

N-[3-(4-Benzyl-4-hydroxy-piperidin-1-yl)-propyl]-4-benzyloxy-benzamide

A mixture of 4-benzyloxy-N-(3-chloro-propyl)-benzamide (0.5 g, 1.64 mmol), ), 4-benzyl-4-hydroxy-piperidine (0.315 g, 1.65 mmol), potassium carbonate (0.45 g, 3.29 mmol) and 2-butanone (10 ml) was stirred at 60° C. for 48 h. After the addition of water, the mixture was extracted with ethyl acetate. The organic layer was dried (Na$_2$SO$_4$), filtered and evaporated. The residue was purified by chromatography (silica gel, methylene chloride-methanol from 95:5 to 9:1) to give N-[3-(4-benzyl-4-hydroxy-piperidin-1-yl)-propyl]-4-benzyloxy-benzamide (185 mg, 25%) as a light yellow solid. MS: me/e=459 (M+H)$^+$.

EXAMPLE 89

4-Benzyloxy-N-[3-[4-hydroxy-4-(4-methyl-benzyl)-piperidin-1-yl]-propyl]-benzamide A mixture of 4-benzyloxy-N-(3-chloro-propyl)-benzamide (0.5 g, 1.64 mmol), ), 4-hydroxy-4-(4-methyl-benzyl)-piperidine (0.34 g, 1.65 mmol), potassium carbonate (0.45 g, 3.29 mmol) and 2-butanone (10 ml) was stirred at 60° C. for 48 h. After the addition of water, the mixture was extracted with ethyl acetate. The organic layer was dried (Na$_2$SO$_4$), filtered and evaporated. The residue was purified by chromatography (silica gel, methylene chloride methanol from 95:5 to 9:1) to give 4-benzyloxy-N-[3-[4-hydroxy-4-(4-methyl-benzyl)-piperidin-1-yl]-propyl]-benzamide (220 mg, 28%) as light yellow solid. MS: me/e =473 (M+H)$^+$.

EXAMPLE 90

1-(2-methylamino-ethyl)-4-(4-methyl-benzyl)-piperidin-4-ol

A mixture of 4-hydroxy-4-(4-methyl-benzyl)-piperidine (1.56 g, 7.6 mmol), sodium carbonate (0.89 g, 8.4 mmol), N-methyl-chloro-acetamide and acetone (14 ml) was stirred at r.t. for 48 h. After evaporation of the solvent, water was added to the slurry. The aqeous layer was extracted with ether, and the organic layer was dried (Na$_2$SO$_4$) filtered and evaporated to give a residue which upon trituration with ether gave 1.3 g of white crystalline material. This was then added portionwise to a stirred suspension of lithium aluminium hydride (350 mg, 9.2 mmol) in THF (30 ml) at 0° C. After stirring overnight at r.t., and heating at reflux temperature for 1 h, the reaction was cooled to 0° C. and water, 15% sodium hydroxide and again water (each time 1 ml) were carefully added. Filtration, evaporation of the solvent from the filtrate, addition of water and extraction with methylene chloride gave after drying (Na$_2$SO$_4$), filtration and evaporation 1-(2-methylamino-ethyl)-4-(4-methyl-benzyl)-piperidin-4-ol (480 mg). MS: me/e=263 (M+H)$^+$.

EXAMPLE 91

4-Benzyloxy-N-[2-[4-hydroxy-4-(4-methyl-benzyl) piperidin-1-yl]-ethyl]-N-methyl-benzamide A mixture of 4-benzyloxy benzoic acid (265 mg, 1.16 mmol), 1,1'-carbonyl-diimidazole (197 mg, 1.21 mmol) and DMF (7 ml) was stirred at 50° C. for 1 h. After cooling to r.t., 1-(2-methylamino-ethyl)-4-(4-methyl-benzyl)-piperidin-4-ol (335 mg, 1.27 mmol) was added and stirring was continued for 1 h. After the addition of water, the mixture was extracted with ether. The organic layer was dried (Na$_2$SO$_4$), filtered and evaporated. The residue was purified by chromatography (silica gel, dichloromethane-methanol 95:5) to give 4-benzyloxy-N-[2-[4-hydroxy-4-(4-methyl-benzyl)-piperidin-1-yl]-ethyl]-N-methyl-benzamide (226 mg) as a pale yellow oil. MS: me/e=473 (M+H)$^+$.

EXAMPLE 92

(E)-1-[4-Hydroxy-4-(4-methyl-benzyl )-piperidin-1-yl]-3-(4-methoxy-phenyl)-propenone A mixture of 4-methoxy cinnamic acid (3.0 g, 16.8 mmol), 1,1'-carbonyl-diimidazole (2.78 g, 1.05 eq.) and DMF (50 ml) is stirred at 50° C. for 1 h. After cooling to r.t., 4-(4methyl-benzyl)-4-hydroxy-piperidine (3.63 g, 1.05 eq.) is added and stirring is continued for 1 h. Water is then added, and the mixture is extracted with ether. Drying (Na$_2$SO$_4$), filtering, and evaporation of the organic layer afforded (E)-1-[4-hydroxy-4-(4-methyl-benzyl)-piperidin-1-yl]-3-(4-methoxy-phenyl)-propenone (5.87 g, 95%) as a white foam. MS: me/e=365 (M)$^+$.

EXAMPLE 93

(E)-1-[4-Hydroxy-4-(4-methyl-benzyl)-piperidin-1-yl]-3-(4-hydroxy-phenyl)-propenone To a solution of (E)-1-[4-hydroxy-4-(4-methyl-benzyl)-piperidin-1-yl]-3-(4-methoxy-phenyl)-propenone (1.68 g, 4.6 mmol) in dichloromethane (50 ml) at 0° C., a 1M boron tribromide in dichloromethane solution (9.2 ml, 2.0 eq.) is added. After stirring at r.t. for 4 h, water (50 ml) and an aqueous sodium bicarbonate solution (20 ml) is added and the aqueous layer is extracted with dichloromethane. The organic layer is dried (Na$_2$SO$_4$), filtered and evaporated to give (E)-1-[4-hydroxy-4-(4-methyl-benzyl)-piperidin-1-yl]-3-(4-hydroxy-phenyl)-propenone (1.423 g, 88%) as a white foam. MS: me/e=351 (M)$^+$.

EXAMPLE 94

(RS )-1-[3-(3-Fluoro-4-hydroxy-phenyl )-2-hydroxy-propyl]-4-(4-methyl-benzyl)- piperidin-4-ol hydrochloride (RS)-1-[3-(3-Fluoro-4-methoxy-phenyl)-2-hydroxy-propyl]-4-(4-methyl-benzyl)-piperidin-4-ol (0.8 g, 2.06 mmol) was dissolved in CH$_2$Cl$_2$ (25 ml) and treated at −10°

C. with BBr$_3$(6.2 ml, 6.2 mmol, 1M in CH$_2$Cl$_2$). Reaction mixture was allowed to warm up to room temperature and stirred for 22 hours. At −10° C., reaction mixture was quenched successively with methanol (MeOH) (10 ml) and sat. NaHCO$_3$ (40 ml). The aqueous phase was extracted with CH$_2$Cl$_2$(3×50 ml), combined organic phases were dried over Na$_2$SO$_4$ and concentrated. The residue was chromatographed over silica gel (CH$_2$Cl$_2$—MeOH 19:1 then 4:1) to provide a white foam which was dissolved in MeOH (5 ml). Addition of 1N HCl (1.2 ml) provided (RS)-1-[3-(3-Fluoro-4-hydroxy-phenyl)-2-hydroxy-propyl]-4-(4-methyl-benzyl)-piperidin-4-ol hydrochloride (0.265 g, 31%) as a white solid mixture of the E/Z isomers, m.p. 207°–209° C. and MS: m/e=374.4 (M+H$^+$).

EXAMPLE 95

(RS)-1-[3-(3-Fluoro-4-methoxy-phenyl)-2-hydroxy-propyl]-4-(4-methyl-benzyl)-piperidin-4-ol (RS)-2-(3-Fluoro-4-methoxy-benzyl)-oxirane (0.48 g, 2.6 mmol) and 4-(4-methyl-benzyl)-piperidin-4-ol (0.65 g, 3.2 mmol) were dissolved in MeOH (3 ml) and stirred at room temperature for 16 hours. Solvent was evaporated and residue was chromatographed over silica gel (CH$_2$Cl$_2$MeOH 19:1) to provide (RS)-1-[3-(3-Fluoro-4-methoxy-phenyl)-2-hydroxy-propyl]-4-(4-methyl-benzyl)-piperidin-4-ol (0.82 g, 81%) as a yellow oil MS: m/e=388.5 (M+H$^+$).

EXAMPLE 96

(RS)-2-(3-Fluoro-4-methoxy-benzyl)-oxirane

4-Allyl-2-fluoro-1-methoxy benzene (1.2 g, 7.22 mmol) was dissolved in CH$_2$Cl$_2$ (35 ml) and treated successively with buffer pH=7.95 (35 ml, NaH$_2$PO$_4$—Na$_2$HPO$_4$) and m-chloroperbenzoic acid 70% (2.2 g, 9 mmol). Reaction mixture was stirred at room temperature for 63 hours. The aqueous phase was extracted with CH$_2$Cl$_2$ (4×30 ml), combined organic phases were washed with sat. NaHCO$_3$ (50 ml), dried over Na$_2$SO$_4$ and concentrated. The residue was chromatographed over siliga gel (hexan-ethyl acetate 9:1) to provide (RS)-2-(3-Fluoro-4-methoxy-benzyl)-oxirane (0.49 g, 37%) as a yellow oil MS: m/e=182 (M$^+$).

EXAMPLE 97

4-Allyl-2-fluoro-1-methoxy-benzene

4-Bromo-2-fluoroanisole (3 g, 14.6 mmol) was dissolved in toluene (100 ml) and treated successively with tetrakis-(triphenylphosphin)-palladium (0.84 g, 0.73 mmol) and allytributylstannane (5.8 ml, 19 mmol). Reaction mixture was refluxed for 23 hours. After evaporation of the solvent, the residue was dissolved in ether (150 ml) and stirred in the presence of sat. KF (20 ml) at room temperature for 0.5 hour. Solid was filtered and H$_2$O (100 ml) was added to the filtrate. The aqueous phase was extracted with ether (2×100 ml), combined organic phases were dried over Na$_2$SO$_4$ and concentrated. The residue was chromatographed over silica gel (hexan-ethyl acetate 19:1) to provide 4-allyl-2-fluoro-1-methoxy-benzene (1.26 g, 52%) as a colorless oil MS: m/e=166 (M$^+$).

EXAMPLE 98

Tablet Formulation (Wet Granulation)

| | | mg/tablet | | | |
|---|---|---|---|---|---|
| Item | Ingredients | 5 mg | 25 mg | 100 mg | 500 mg |
| 1. | Compound of formula 1 | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 835 |

Manufacturing Procedure

1. Mix items 1, 2, 3 and 4 and granulate with purified water.
2. Dry the granulation at 50° C.
3. Pass the granulation through suitable milling equipment.
4. Add item 5 and mix for three minutes; compress on a suitable press.

EXAMPLE 99

Capsule Formulation

| | | mg/tablet | | | |
|---|---|---|---|---|---|
| Item | Ingredients | 5 mg | 25 mg | 100 mg | 500 mg |
| 1. | Compound of formula 1 | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure

1. Mix items 1, 2, and 3 in a suitable mixer for 30 minutes.
2. Add items 4 and 5 and mix for 3 minutes.
3. Fill into a suitable capsule.
4. Add item 5 and mix for three minutes; compress on a suitable press.

We claim:

1. A compound of the formula

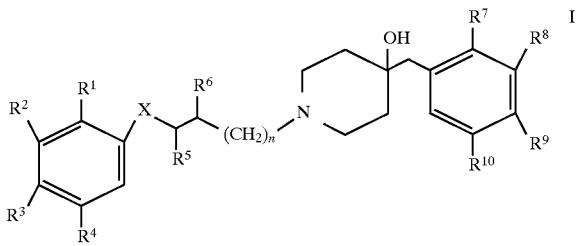

wherein x is —O—, —NH—, —CH$_2$—, —CH=, —CO$_2$—, —CONH—, or —CON(lower alkyl)—;

R$^1$–R$^4$ are, independently, hydrogen, halogen, hydroxy, amino, nitro, lower-alkyl-sulfonylamido, 1- or 2-imidazolyl, 1-(1,2,4-triazolyl) or acetamido;

R$^5$, R$^6$ are, independently, hydrogen, lower-alkyl, hydroxy, lower alkoxy or oxo;

R$^7$–R$^{10}$ are, independently, hydrogen, lower-alkyl, halogen, trifluoromethyl or lower-alkoxy;

n is 0 or 1;

or pharmaceutically acceptable acid addition salt thereof.

2. A compound according to claim 1, wherein X is —O—.

3. A compound according to claim 2, wherein $R^1$ is hydrogen, $R^2$ is hydrogen, $R^3$ is hydroxy or lower alkyl-sulfonylamido, $R^4$ is hydrogen, $R^5$ is hydrogen, $R^6$ is hydroxy, hydrogen or lower alkyl, $R^7$ is hydrogen, $R^8$ is hydrogen, $R^9$ is hydrogen, lower alkyl or halogen, $R^{10}$ is hydrogen and n is 0 or 1.

4. A compound according to claim 1 selected from the following group:
1-[2-(4-hydroxy-phenoxy)-ethyl]-4-(4-methyl-benzyl)-piperidin-4-ol;
4-(4-fluoro-benzyl)-1-[2-(4-hydroxy-phenoxy)-ethyl]-piperidin-4-ol;
N-(4-{2-[4-hydroxy-4-(4-methyl-benzyl)-piperidin-1-yl]-ethoxy}-phenyl)-methanesulfonamide;
N-(4-{2-[4-(4-fluoro-benzyl)-4-hydroxy-piperidin-1-yl]-ethoxy}-phenyl)-methanesulfonamide;
N-(4-{2-[4-(4-chloro-benzyl)-4-hydroxy-piperidin-1-yl]-ethoxy}-phenyl)-methanesulfonamide;
N-(4-{3-[4-(4-fluoro-benzyl)-4-hydroxy-piperidin-1-yl]-propoxy}-phenyl)-methanesulfonamide; and
1-[2-(4-hydroxy-phenoxy)-1-methyl-ethyl]-4-(4-methyl-benzyl)-piperidin-4-ol.

5. A compound according to claim 1, wherein X is —NH—.

6. A compound according to claim 5, wherein $R^1$, $R^2$, $R^4$, $R^6$, $R^7$, $R^8$ and $R^{10}$ are hydrogen, $R^3$ is hydroxy, $R^5$ is oxo, $R^9$ is hydrogen or lower alkyl and n is 0 or 1.

7. A compound according to claim 6 selected from the group consisting of
2-(4-benzyl-4-hydroxy-piperidin-1-yl)-N-(4-hydroxy-phenyl)-acetamide and
2-[4-hydroxy-4-(4-methyl-benzyl)-piperidin-1-yl]-N-(4-hydroxy-phenyl)-acetamide.

8. A compound according to claim 1, wherein X is —CH$_2$—.

9. A compound according to claim 8, wherein $R^1$, $R^2$, $R^4$, $R^6$, $R^7$, $R^8$ and $R^{10}$ are hydrogen, $R^3$ is hydroxy, $R^5$ is hydroxy, $R^9$ is hydrogen or lower alkyl and n is 0.

10. A compound according to claim 9 selected from the following group:
(RS)-4-benzyl-1-[2-hydroxy-3-(4-hydroxy-phenyl)-propyl]-piperidin-4-ol;
(RS)-1-[2-hydroxy-3-(4-hydroxy-phenyl)-propyl]-4-(4-methyl-benzyl)-piperidin-4-ol; and
(RS)-4-(4-chloro-benzyl)-1-[2-hydroxy-3-(4-hydroxy-phenyl)-propyl]-piperidin-4-ol.

11. A compound according to claim 1, wherein X is —CH=.

12. A compound according to claim 1, wherein X is —CO$_2$—.

13. A compound according to claim 1, wherein X is —CONH—.

14. A compound according to claim 1, wherein X is —CON(lower alkyl).

15. A pharmaceutical composition comprising an effective amount of a compound of the formula

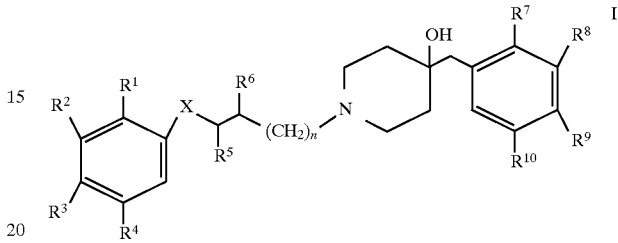

wherein
X is —O—, —NH—, —CH$_2$—, —CH=, —CO$_2$—, —CONH—, or —CON(lower alkyl)—;
$R^1$–$R^4$ are, independently, hydrogen, halogen, hydroxy, amino, nitro, lower-alkyl-sulfonylamido, 1- or 2-imidazolyl, 1-(1,2,4-triazolyl) or acetamido;
$R^5$, $R^6$ are, independently, hydrogen, lower-alkyl, hydroxy, lower alkoxy or oxo;
$R^7$–$R^{10}$ are, independently, hydrogen, lower-alkyl, halogen, trifluoromethyl or lower-alkoxy;
n is 0 or 1;
and a therapeutically inert carrier.

16. The composition of claim 15, wherein in the compound of formula IX is —O—.

17. The composition of claim 15, wherein in the compound of formula IX is —NH—.

18. The composition of claim 15, wherein in the compound of formula IX is —CH$_2$—.

19. The composition of claim 15, wherein in the compound of formula IX is —CH=.

20. The composition of claim 15, wherein in the compound of formula IX is —CO$_2$—.

21. The composition of claim 15, wherein in the compound of formula IX is —CONH—.

22. The composition of claim 15, wherein in the compound of formula IX is —CON(lower alkyl).

* * * * *